(12) United States Patent
Lanphere et al.

(10) Patent No.: US 7,964,123 B2
(45) Date of Patent: *Jun. 21, 2011

(54) EMBOLIZATION

(75) Inventors: Janel L. Lanphere, Flagstaff, AZ (US); Marcia S. Buiser, Watertown, MA (US); Thomas V. Casey, Grafton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/652,552

(22) Filed: Jan. 5, 2010

(65) Prior Publication Data

US 2010/0109178 A1    May 6, 2010

Related U.S. Application Data

(63) Continuation of application No. 11/923,009, filed on Oct. 24, 2007, now Pat. No. 7,666,333, which is a continuation of application No. 10/858,253, filed on Jun. 1, 2004, now Pat. No. 7,311,861.

(51) Int. Cl.
*B29B 9/10* (2006.01)
(52) U.S. Cl. ..................... 264/5; 264/7; 264/9
(58) Field of Classification Search .................. None
See application file for complete search history.

(56) References Cited

U.S. PATENT DOCUMENTS

| | | |
|---|---|---|
| 2,275,154 A | 3/1942 | Merrill et al. |
| 2,609,347 A | 9/1952 | Wilson |
| 3,663,470 A | 5/1972 | Nishimura et al. |
| 3,737,398 A | 6/1973 | Yamaguchi |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,402,319 A | 9/1983 | Handa et al. |
| 4,413,070 A | 11/1983 | Rembaum |
| 4,427,794 A | 1/1984 | Lange et al. |
| 4,428,869 A | 1/1984 | Munteanu et al. |

(Continued)

FOREIGN PATENT DOCUMENTS

AU    76186/98    10/1998

(Continued)

OTHER PUBLICATIONS

"Fibroid Treatment Collective—Fibroid Embolization," 2 pages, http://www.fibroids.org.

(Continued)

*Primary Examiner* — Mary Lynn F Theisen
(74) *Attorney, Agent, or Firm* — Fish & Richardson P.C.

(57) ABSTRACT

Embolization, as well as related particles and methods, are described.

31 Claims, 12 Drawing Sheets

U.S. PATENT DOCUMENTS

| | | |
|---|---|---|
| 4,429,062 A | 1/1984 | Pasztor et al. |
| 4,442,843 A | 4/1984 | Rasor et al. |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor et al. |
| 4,492,720 A | 1/1985 | Moiser |
| 4,515,906 A | 5/1985 | Friesen et al. |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |
| 4,573,967 A | 3/1986 | Hargrove et al. |
| 4,622,362 A | 11/1986 | Rembaum |
| 4,623,706 A | 11/1986 | Timm et al. |
| 4,629,464 A | 12/1986 | Takata et al. |
| 4,640,807 A | 2/1987 | Afghan et al. |
| 4,657,756 A | 4/1987 | Rasor et al. |
| 4,661,137 A | 4/1987 | Garnier et al. |
| 4,663,358 A | 5/1987 | Hyon et al. |
| 4,671,954 A | 6/1987 | Goldberg et al. |
| 4,671,994 A | 6/1987 | Cochran, Jr. |
| 4,674,480 A | 6/1987 | Lemelson |
| 4,675,113 A | 6/1987 | Graves et al. |
| 4,678,710 A | 7/1987 | Sakimoto et al. |
| 4,678,814 A | 7/1987 | Rembaum |
| 4,680,320 A | 7/1987 | Uku et al. |
| 4,681,119 A | 7/1987 | Rasor et al. |
| 4,695,466 A | 9/1987 | Morishita et al. |
| 4,713,076 A | 12/1987 | Draenert |
| 4,742,086 A | 5/1988 | Masamizu et al. |
| 4,743,507 A | 5/1988 | Franses et al. |
| 4,772,635 A | 9/1988 | Mitschker et al. |
| 4,782,097 A | 11/1988 | Jain et al. |
| 4,789,501 A | 12/1988 | Day et al. |
| 4,793,980 A | 12/1988 | Torobin |
| 4,795,741 A | 1/1989 | Leshchiner et al. |
| 4,801,458 A | 1/1989 | Hidaka et al. |
| 4,804,366 A | 2/1989 | Zdeb et al. |
| 4,819,637 A | 4/1989 | Dormandy, Jr. et al. |
| 4,822,535 A | 4/1989 | Ekman et al. |
| 4,833,237 A | 5/1989 | Kawamura et al. |
| 4,850,978 A | 7/1989 | Dudar et al. |
| 4,859,711 A | 8/1989 | Jain et al. |
| 4,863,972 A | 9/1989 | Itagaki et al. |
| 4,897,255 A | 1/1990 | Fritzberg et al. |
| 4,929,400 A | 5/1990 | Rembaum et al. |
| 4,933,372 A | 6/1990 | Feibush et al. |
| 4,946,899 A | 8/1990 | Kennedy et al. |
| 4,954,399 A | 9/1990 | Tani et al. |
| 4,981,625 A | 1/1991 | Rhim et al. |
| 4,990,340 A | 2/1991 | Hidaka et al. |
| 4,999,188 A | 3/1991 | Sloldovnik et al. |
| 5,007,940 A | 4/1991 | Berg |
| 5,011,677 A | 4/1991 | Day et al. |
| H915 H | 5/1991 | Gibbs |
| 5,015,423 A | 5/1991 | Eguchi et al. |
| 5,032,117 A | 7/1991 | Motta |
| 5,034,324 A | 7/1991 | Shinozaki et al. |
| 5,047,438 A | 9/1991 | Feibush et al. |
| 5,079,274 A | 1/1992 | Schneider et al. |
| 5,091,205 A | 2/1992 | Fan |
| 5,106,903 A | 4/1992 | Vanderhoff et al. |
| 5,114,421 A | 5/1992 | Polak |
| 5,116,387 A | 5/1992 | Berg |
| 5,120,349 A | 6/1992 | Stewart et al. |
| 5,125,892 A | 6/1992 | Drudik |
| 5,147,631 A | 9/1992 | Glajch et al. |
| 5,147,937 A | 9/1992 | Frazza et al. |
| 5,149,543 A | 9/1992 | Cohen et al. |
| 5,158,573 A | 10/1992 | Berg |
| 5,171,214 A | 12/1992 | Kolber et al. |
| 5,171,217 A | 12/1992 | March et al. |
| 5,181,921 A | 1/1993 | Makita et al. |
| 5,190,760 A | 3/1993 | Baker |
| 5,190,766 A | 3/1993 | Ishihara |
| 5,192,301 A | 3/1993 | Kamiya et al. |
| 5,202,352 A | 4/1993 | Okada et al. |
| 5,216,096 A | 6/1993 | Hattori et al. |
| 5,236,410 A | 8/1993 | Granov et al. |
| 5,253,991 A | 10/1993 | Yokota et al. |
| 5,260,002 A | 11/1993 | Wang |
| 5,262,176 A | 11/1993 | Palmacci et al. |
| 5,263,992 A | 11/1993 | Guire |
| 5,288,763 A | 2/1994 | Li et al. |
| 5,292,814 A | 3/1994 | Bayer et al. |
| 5,302,369 A | 4/1994 | Day et al. |
| 5,314,974 A | 5/1994 | Ito et al. |
| 5,316,774 A | 5/1994 | Eury et al. |
| RE34,640 E | 6/1994 | Kennedy et al. |
| 5,320,639 A | 6/1994 | Rudnick |
| 5,328,936 A | 7/1994 | Leifholtz et al. |
| 5,336,263 A | 8/1994 | Ersek et al. |
| 5,344,452 A | 9/1994 | Lemperle |
| 5,344,867 A | 9/1994 | Morgan et al. |
| 5,354,290 A | 10/1994 | Gross |
| 5,369,133 A | 11/1994 | Ihm et al. |
| 5,369,163 A | 11/1994 | Chiou et al. |
| 5,382,260 A | 1/1995 | Dormandy, Jr. et al. |
| 5,384,124 A | 1/1995 | Courteille et al. |
| 5,397,303 A | 3/1995 | Sancoff et al. |
| 5,398,851 A | 3/1995 | Sancoff et al. |
| 5,403,870 A | 4/1995 | Gross |
| 5,417,982 A | 5/1995 | Modi |
| 5,431,174 A | 7/1995 | Knute |
| 5,435,645 A | 7/1995 | Faccioli et al. |
| 5,441,746 A | 8/1995 | Chagnon |
| 5,443,495 A | 8/1995 | Buscemi et al. |
| 5,456,693 A | 10/1995 | Conston et al. |
| 5,468,801 A | 11/1995 | Antonelli et al. |
| 5,469,854 A | 11/1995 | Unger et al. |
| 5,476,472 A | 12/1995 | Dormandy, Jr. et al. |
| 5,484,584 A | 1/1996 | Wallace et al. |
| 5,490,984 A | 2/1996 | Freed |
| 5,494,682 A | 2/1996 | Cohen et al. |
| 5,494,940 A | 2/1996 | Unger et al. |
| 5,512,604 A | 4/1996 | Demopolis |
| 5,514,090 A | 5/1996 | Kriesel et al. |
| 5,514,379 A | 5/1996 | Weissleder et al. |
| 5,525,334 A | 6/1996 | Ito et al. |
| 5,534,589 A | 7/1996 | Hager et al. |
| 5,541,031 A | 7/1996 | Yamashita et al. |
| 5,542,935 A | 8/1996 | Unger et al. |
| 5,553,741 A | 9/1996 | Sancoff et al. |
| 5,556,391 A | 9/1996 | Cercone et al. |
| 5,556,610 A | 9/1996 | Yan et al. |
| 5,558,255 A | 9/1996 | Sancoff et al. |
| 5,558,822 A | 9/1996 | Gitman et al. |
| 5,558,856 A | 9/1996 | Klaveness et al. |
| 5,559,266 A | 9/1996 | Klaveness et al. |
| 5,567,415 A | 10/1996 | Porter |
| 5,569,193 A | 10/1996 | Hofstetter et al. |
| 5,569,449 A | 10/1996 | Klaveness et al. |
| 5,569,468 A | 10/1996 | Modi |
| 5,571,182 A | 11/1996 | Ersek et al. |
| 5,580,575 A | 12/1996 | Unger et al. |
| 5,583,162 A | 12/1996 | Li et al. |
| 5,585,112 A | 12/1996 | Unger et al. |
| 5,595,821 A | 1/1997 | Hager et al. |
| 5,622,657 A | 4/1997 | Takada et al. |
| 5,624,685 A | 4/1997 | Takahashi et al. |
| 5,635,215 A | 6/1997 | Boschetti et al. |
| 5,637,087 A | 6/1997 | O'Neil et al. |
| 5,639,710 A | 6/1997 | Lo et al. |
| 5,648,095 A | 7/1997 | Illum et al. |
| 5,648,100 A | 7/1997 | Boschetti et al. |
| 5,650,116 A | 7/1997 | Thompson |
| 5,651,990 A | 7/1997 | Takada et al. |
| 5,653,922 A | 8/1997 | Li et al. |
| 5,657,756 A | 8/1997 | Vrba |
| 5,662,840 A | 9/1997 | Thomas et al. |
| 5,681,576 A | 10/1997 | Henry |
| 5,695,480 A | 12/1997 | Evans et al. |
| 5,695,740 A | 12/1997 | Porter |
| 5,698,271 A | 12/1997 | Liberti et al. |

| Patent No. | Date | Inventor |
|---|---|---|
| 5,701,899 A | 12/1997 | Porter |
| 5,715,824 A | 2/1998 | Unger et al. |
| 5,716,981 A | 2/1998 | Hunter et al. |
| 5,718,884 A | 2/1998 | Klaveness et al. |
| 5,723,269 A | 3/1998 | Akagi et al. |
| 5,725,534 A | 3/1998 | Rasmussen |
| 5,733,925 A | 3/1998 | Kunz et al. |
| 5,736,074 A | 4/1998 | Hayes et al. |
| 5,741,331 A | 4/1998 | Pinchuk |
| 5,746,734 A | 5/1998 | Dormandy, Jr. et al. |
| 5,752,974 A | 5/1998 | Rhee et al. |
| 5,756,127 A | 5/1998 | Grisoni et al. |
| 5,760,097 A | 6/1998 | Li et al. |
| 5,766,147 A | 6/1998 | Sancoff et al. |
| 5,770,222 A | 6/1998 | Unger et al. |
| 5,779,668 A | 7/1998 | Grabenkort |
| 5,785,642 A | 7/1998 | Wallace et al. |
| 5,785,682 A | 7/1998 | Grabenkort |
| 5,792,478 A | 8/1998 | Lawin et al. |
| 5,795,562 A | 8/1998 | Klaveness et al. |
| 5,797,953 A | 8/1998 | Tekulve |
| 5,807,323 A | 9/1998 | Kriesel et al. |
| 5,813,411 A | 9/1998 | Van Bladel et al. |
| 5,823,198 A | 10/1998 | Jones et al. |
| 5,827,502 A | 10/1998 | Klaveness et al. |
| 5,827,531 A | 10/1998 | Morrison et al. |
| 5,830,178 A | 11/1998 | Jones et al. |
| 5,833,361 A | 11/1998 | Funk |
| 5,840,387 A | 11/1998 | Berlowitz-Tarrant et al. |
| 5,846,518 A | 12/1998 | Yan et al. |
| 5,853,752 A | 12/1998 | Unger et al. |
| 5,855,615 A | 1/1999 | Bley et al. |
| 5,863,957 A | 1/1999 | Li et al. |
| 5,876,372 A | 3/1999 | Grabenkort et al. |
| 5,877,224 A | 3/1999 | Brocchini et al. |
| 5,885,216 A | 3/1999 | Evans, III et al. |
| 5,885,547 A | 3/1999 | Gray |
| 5,888,546 A | 3/1999 | Ji et al. |
| 5,888,930 A | 3/1999 | Smith et al. |
| 5,891,155 A | 4/1999 | Irie |
| 5,894,022 A | 4/1999 | Ji et al. |
| 5,895,398 A | 4/1999 | Wensel et al. |
| 5,895,411 A | 4/1999 | Irie |
| 5,899,877 A | 5/1999 | Leibitzki et al. |
| 5,902,832 A | 5/1999 | Van Bladel et al. |
| 5,902,834 A | 5/1999 | Porrvik |
| 5,922,025 A | 7/1999 | Hubbard |
| 5,922,304 A | 7/1999 | Unger |
| 5,928,626 A | 7/1999 | Klaveness et al. |
| 5,935,553 A | 8/1999 | Unger et al. |
| 5,951,160 A | 9/1999 | Ronk |
| 5,957,848 A | 9/1999 | Sutton et al. |
| 5,959,073 A | 9/1999 | Schlameus et al. |
| 6,003,566 A | 12/1999 | Thibault et al. |
| 6,015,546 A | 1/2000 | Sutton et al. |
| 6,027,472 A | 2/2000 | Kriesel et al. |
| 6,028,066 A | 2/2000 | Unger |
| 6,047,861 A | 4/2000 | Vidal et al. |
| 6,048,908 A | 4/2000 | Kitagawa |
| 6,051,247 A | 4/2000 | Hench et al. |
| 6,056,721 A | 5/2000 | Shulze |
| 6,056,844 A | 5/2000 | Guiles et al. |
| 6,059,766 A | 5/2000 | Greff |
| 6,063,068 A | 5/2000 | Fowles et al. |
| 6,071,495 A | 6/2000 | Unger et al. |
| 6,071,497 A | 6/2000 | Steiner et al. |
| 6,073,759 A | 6/2000 | Lamborne et al. |
| 6,090,925 A | 7/2000 | Woiszwillo et al. |
| 6,096,344 A | 8/2000 | Liu et al. |
| 6,099,064 A | 8/2000 | Lund |
| 6,099,864 A | 8/2000 | Morrison et al. |
| 6,100,306 A | 8/2000 | Li et al. |
| 6,139,963 A | 10/2000 | Fujii et al. |
| 6,149,623 A | 11/2000 | Reynolds |
| 6,160,084 A | 12/2000 | Langer et al. |
| 6,162,377 A | 12/2000 | Ghosh et al. |
| 6,165,193 A | 12/2000 | Greene, Jr. et al. |
| 6,167,313 A | 12/2000 | Gray et al. |
| 6,179,817 B1 | 1/2001 | Zhong |
| 6,191,193 B1 | 2/2001 | Lee et al. |
| 6,214,331 B1 | 4/2001 | Vanderhoff et al. |
| 6,214,384 B1 | 4/2001 | Pallado et al. |
| 6,224,630 B1 | 5/2001 | Bao et al. |
| 6,224,794 B1 | 5/2001 | Amsden et al. |
| 6,235,224 B1 | 5/2001 | Mathiowitz et al. |
| 6,238,403 B1 | 5/2001 | Greene, Jr. et al. |
| 6,245,090 B1 | 6/2001 | Gilson et al. |
| 6,251,661 B1 | 6/2001 | Urabe et al. |
| 6,258,338 B1 | 7/2001 | Gray |
| 6,261,585 B1 | 7/2001 | Sefton et al. |
| 6,264,861 B1 | 7/2001 | Tavernier et al. |
| 6,267,154 B1 | 7/2001 | Felicelli et al. |
| 6,268,053 B1 | 7/2001 | Woiszwillo et al. |
| 6,277,392 B1 | 8/2001 | Klein |
| 6,280,457 B1 | 8/2001 | Wallace et al. |
| 6,291,605 B1 | 9/2001 | Freeman et al. |
| 6,296,604 B1 | 10/2001 | Garibaldi et al. |
| 6,296,622 B1 | 10/2001 | Kurz et al. |
| 6,296,632 B1 | 10/2001 | Luscher et al. |
| 6,306,418 B1 | 10/2001 | Bley |
| 6,306,419 B1 | 10/2001 | Vachon et al. |
| 6,306,425 B1 | 10/2001 | Tice et al. |
| 6,306,427 B1 | 10/2001 | Annonier et al. |
| 6,312,407 B1 | 11/2001 | Zadno-Azizi et al. |
| 6,312,942 B1 | 11/2001 | Plüss-Wenzinger et al. |
| 6,315,709 B1 | 11/2001 | Garibaldi et al. |
| 6,335,384 B1 | 1/2002 | Evans et al. |
| 6,344,182 B1 | 2/2002 | Sutton et al. |
| 6,355,275 B1 | 3/2002 | Klein |
| 6,368,658 B1 | 4/2002 | Schwarz et al. |
| 6,379,373 B1 | 4/2002 | Sawhney et al. |
| 6,388,043 B1 | 5/2002 | Langer et al. |
| 6,394,965 B1 | 5/2002 | Klein |
| 6,410,508 B1 | 6/2002 | Isales et al. |
| 6,423,332 B1 | 7/2002 | Huxel et al. |
| 6,432,437 B1 | 8/2002 | Hubbard |
| 6,436,112 B2 | 8/2002 | Wensel et al. |
| 6,443,941 B1 | 9/2002 | Slepian et al. |
| 6,458,296 B1 | 10/2002 | Heinzen et al. |
| 6,476,069 B2 | 11/2002 | Krall et al. |
| 6,495,155 B1 | 12/2002 | Tice et al. |
| 6,544,503 B1 | 4/2003 | Vanderhoff et al. |
| 6,544,544 B2 | 4/2003 | Hunter et al. |
| 6,545,097 B2 | 4/2003 | Pinchuk et al. |
| 6,565,887 B1 | 5/2003 | Gray et al. |
| 6,575,896 B2 | 6/2003 | Silverman et al. |
| 6,586,364 B2 | 7/2003 | Kubota et al. |
| 6,602,261 B2 | 8/2003 | Greene, Jr. et al. |
| 6,602,524 B2 | 8/2003 | Batich et al. |
| 6,605,111 B2 | 8/2003 | Bose et al. |
| 6,629,947 B1 | 10/2003 | Sahatjian et al. |
| 6,632,531 B2 | 10/2003 | Blankenship |
| 6,652,883 B2 | 11/2003 | Goupil et al. |
| 6,680,046 B1 | 1/2004 | Boschetti |
| 6,699,222 B1 | 3/2004 | Jones et al. |
| 6,706,394 B2 | 3/2004 | Kuehnle et al. |
| 7,356,368 B2 | 4/2008 | Tan |
| 7,591,993 B2 | 9/2009 | Boschetti |
| 2001/0001835 A1 | 5/2001 | Greene, Jr. et al. |
| 2001/0016210 A1 | 8/2001 | Mathiowitz et al. |
| 2001/0036451 A1 | 11/2001 | Goupil et al. |
| 2001/0051670 A1 | 12/2001 | Goupil et al. |
| 2002/0054912 A1 | 5/2002 | Kim et al. |
| 2002/0061954 A1 | 5/2002 | Davis et al. |
| 2002/0160109 A1 | 10/2002 | Yeo et al. |
| 2002/0182190 A1 | 12/2002 | Naimark et al. |
| 2002/0197208 A1 | 12/2002 | Ruys et al. |
| 2003/0007928 A1 | 1/2003 | Gray |
| 2003/0032935 A1 | 2/2003 | Damiano et al. |
| 2003/0108614 A1 | 6/2003 | Volkonsky et al. |
| 2003/0163187 A1 | 8/2003 | Weber |
| 2003/0183962 A1 | 10/2003 | Buiser et al. |
| 2003/0185895 A1 | 10/2003 | Lanphere et al. |
| 2003/0185896 A1 | 10/2003 | Buiser et al. |
| 2003/0187320 A1 | 10/2003 | Freyman |
| 2003/0194390 A1 | 10/2003 | Krall et al. |
| 2003/0203985 A1 | 10/2003 | Baldwin et al. |
| 2003/0206864 A1 | 11/2003 | Mangin |

| | | | |
|---|---|---|---|
| 2003/0215519 A1 | 11/2003 | Schwarz et al. | |
| 2003/0233150 A1 | 12/2003 | Bourne et al. | |
| 2004/0076582 A1 | 4/2004 | DiMatteo et al. | |
| 2004/0091543 A1 | 5/2004 | Bell et al. | |
| 2004/0092883 A1 | 5/2004 | Casey, III et al. | |
| 2004/0096662 A1 | 5/2004 | Lanphere et al. | |
| 2004/0101564 A1 | 5/2004 | Rioux et al. | |
| 2004/0186377 A1 | 9/2004 | Zhong et al. | |
| 2005/0025800 A1 | 2/2005 | Tan | |
| 2005/0037047 A1 | 2/2005 | Song | |
| 2005/0095428 A1 | 5/2005 | DiCarlo et al. | |
| 2005/0129775 A1 | 6/2005 | Lanphere et al. | |
| 2005/0196449 A1 | 9/2005 | DiCarlo et al. | |
| 2005/0226935 A1 | 10/2005 | Kamath et al. | |
| 2005/0238870 A1 | 10/2005 | Buiser et al. | |
| 2007/0110786 A1 | 5/2007 | Tenney et al. | |

FOREIGN PATENT DOCUMENTS

| | | |
|---|---|---|
| DE | 3834705 | 4/1990 |
| DE | 42 01 461 | 7/1993 |
| DE | 94 14 868.6 | 2/1995 |
| DE | 297 24 255 | 10/2000 |
| DE | 100 26 620 | 3/2002 |
| EP | 0 067 459 | 12/1982 |
| EP | 0 122 624 | 10/1984 |
| EP | 0 123 235 | 10/1984 |
| EP | 0 243 165 | 10/1987 |
| EP | 0 294 206 | 12/1988 |
| EP | 0 422 258 | 10/1989 |
| EP | 0 402 031 | 5/1990 |
| EP | 0 458 079 | 11/1991 |
| EP | 0 458 745 | 11/1991 |
| EP | 0 470 569 | 2/1992 |
| EP | 0 547 530 | 6/1993 |
| EP | 0 600 529 | 12/1993 |
| EP | 0 623 012 | 11/1994 |
| EP | 0 706 376 | 4/1996 |
| EP | 0 730 847 | 9/1996 |
| EP | 0 744 940 | 12/1996 |
| EP | 0 797 988 | 10/1997 |
| EP | 0 067 459 | 3/1998 |
| EP | 0 764 047 | 8/2003 |
| EP | 0 993 337 | 4/2004 |
| ES | 2 096 521 | 3/1997 |
| JP | 59-196738 | 11/1984 |
| JP | 62-45637 | 2/1987 |
| JP | 4-74117 | 3/1992 |
| JP | 6-57012 | 3/1994 |
| JP | 9-110678 | 4/1997 |
| JP | 9-165328 | 6/1997 |
| JP | 9-316271 | 12/1997 |
| JP | 10-130329 | 5/1998 |
| JP | 2000189511 | 7/2000 |
| JP | 2001079011 | 3/2001 |
| JP | 2002 017848 | 1/2002 |
| NZ | 255409 | 2/1997 |
| NZ | 517377 | 8/2003 |
| TW | 421658 | 2/2001 |
| WO | 91/12823 | 5/1991 |
| WO | 92/21327 | 12/1992 |
| WO | 93/00063 | 1/1993 |
| WO | 93/19702 | 10/1993 |
| WO | 94/10936 | 5/1994 |
| WO | 95/03036 | 2/1995 |
| WO | 95/22318 | 8/1995 |
| WO | 95/33553 | 12/1995 |
| WO | 96/37165 | 11/1996 |
| WO | 96/39464 | 12/1996 |
| WO | 98/04616 | 2/1998 |
| WO | 98/10798 | 3/1998 |
| WO | 98/26737 | 6/1998 |
| WO | 98/47532 | 10/1998 |
| WO | 99/00187 | 1/1999 |
| WO | 99/12577 | 3/1999 |
| WO | 99/43380 | 9/1999 |
| WO | 99/51278 | 10/1999 |
| WO | 99/57176 | 11/1999 |
| WO | 00/23054 | 4/2000 |
| WO | 00/32112 | 6/2000 |
| WO | 00/40259 | 7/2000 |
| WO | 00/66183 | 11/2000 |
| WO | 00/71196 | 11/2000 |
| WO | 00/74633 | 12/2000 |
| WO | 01/12359 | 2/2001 |
| WO | 01/66016 | 9/2001 |
| WO | 01/70291 | 9/2001 |
| WO | 01/72281 | 10/2001 |
| WO | 01/76845 | 10/2001 |
| WO | 01/93920 | 12/2001 |
| WO | 02/11696 | 2/2002 |
| WO | 02/34298 | 5/2002 |
| WO | 02/34299 | 5/2002 |
| WO | 02/34300 | 5/2002 |
| WO | 02/43580 | 6/2002 |
| WO | 03/013552 | 2/2003 |
| WO | 03/016364 | 2/2003 |
| WO | 03/051451 | 6/2003 |
| WO | 03/082359 | 9/2003 |
| WO | 2004/019999 | 3/2004 |
| WO | 2004/020042 | 3/2004 |
| WO | 2004/040972 | 5/2004 |
| WO | 2004/073688 | 9/2004 |
| WO | 2004/075989 | 9/2004 |

OTHER PUBLICATIONS

"Injectable Tissue Implant Could Repair Ravages of Surgery", Clemson University, Biotech Week, Oct. 22, 2003, p. 117.

"Pulmonary artery pseudoaneurysm/aneurysm".

Available Web Site: http://www.mamc.amedd.army.mil/williams/chest/vascular/paanaeurysm/paaneyrysm.htm.

"Smart Sutures Tie Themselves", Apr. 26, 2002, http://www.sciam.com/article.cfm?articleID=00047706-121F-1CD0-B4A8809EC588, 2 pages.

Abbara et al., "Transcervical Expulsion of a Fibroid as a Result of Uterine Artery Embolization for Leiomyomata", JVIR, vol. 10, No. 4, pp. 409-411, 1999.

Abrahams, J.M. et al., "Delivery of Human Vascular Endothelial Growth Factor with Platinum Coils Enhances Wall Thickening and Coil Impregnation in a Rat Aneurysm Model", AJNR Am. J. Neuroradiol. 22:1410-1417, Aug. 2001.

Abrahams, J.M. et al., "Topic Review: Surface Modifications Enhancing Biological Activity of Guglielmi Detachable Coils in Treating Intracranial Aneurysms", Surg. Neurol. 54:34-41, 2000.

Ahuja, A.A., "Platinum Coil Coatings to Increase Thrombogenicity: A Preliminary Study in Rabbits", AJNR Am. J. Neuroradiol. 14:794-798; Jul./Aug. 1993.

Antibody Labeling, http://www.altcorp.com/AffinityLabeling/ablaeling.htm, pp. 1-6, May 20, 2003.

Bachtsi, A.R. et al., "An Experimental Investigation of Enzyme Release from Poly(vinyl alcohol) crosslinked Microspheres", J. Microencapsulation, vol. 12, No. 1, pp. 23-35; 1995.

Barr, J.D., et al., "Polyvinyl Alcohol Foam Particles Sizes and Concentrations Injectable through Microcatheters", JVIR, vol. 9, No. 1, pp. 113-118; 1998.

Barton, P. et al., "Embolization f Bone Metastases", Journal of Vascular and Interventional Radiology, vol. 7, No. 1, Jan.-Feb. 1996, p. 81-88.

Barttinelli, L. et al., "New Class of Poly(vinyl alcohol) Polymrs as Column-Chromatography Stationary Phases for *Candida rugosa* Lipase Isoforms Separation.", J. Chromatogr A, vol. 753, No. 1, pp. 47-55; 1996. Abstract. http://www.ncbi.nlm.nih.gov/entrez/query.fcgi?.

Beaujeux, R. et al., "Trisacryl Gelatin Microspheres for Therapeutic Embolization, II: Preliminary Clinical Evaluation in Tumors and Arteriovenous Malformations," AJNR Am. J. Neuroradiol. 17:541-548, Mar. 1996.

Berenstein, A. et al., "Catheter and Material Selection for Transarterial Embolization: Technical Considerations. II. Materials.", Radiology, vol. 132, No. 3, pp. 631-639; 1979.

Berenstein, A. et al., "Microembolization Techniques of Vascular Occlusion: Radiologic, Patohologic, and Clinical Correlation", AJNR Am I Neuroradiol, vol. 2, No. 3, pp. 261-267; 1981. Abstract, http://www.ncbi.nlm.nih.gov/entrez/query.fcgi?.

Berkowitz, R.P. et al., "Vaginal Expulsion of Submucosal Fibroids After Uterine Artery Embolization", Journal of Reproductive Medicine, vol. 44, No. 4, pp. 373-376; Apr. 1999.
http://www.reproductivemedicine.com.
Bourke et al., "Protein Drug Release from Photocrosslinked Poly(vinyl alcohol) Hydrogels," Society for Biomaterials 28th Annual Meeting Transactions, p. 144 (2002).
Bradley, E.A. et al., "Transcatheter Uterine Artery Embolisation to Treat Large Uterine Fibroids", British Journal of Obstetrics and Gynaecology, vol. 105, pp. 235-240; Feb. 1998.
Brockmann, J. et al., "Radiolabeling of p-Bz-DOTA-CD-11c antibody with 88Y: Conjugation, Labeling, Biodistribution studies", 2 pages, 2000.
http://www.kernchemie.uni-mainz.de/downloads/jb2000/b14_brockmann.pdf.
Bruix, J. et al., "Transarterial Embolization Versus Symptomatic Treatment in Patients With Advanced Hepatocellular Carcinoma: Results of a Randomized, Controlled Trial in a Single Institution", Hepatology, Jun. 1998, vol. 27, No. 6, pp. 1578-1583.
Available Web Site: http://www.hepatitis-central.com/hcv/hcc/embolization/references.html.
Buhle, Jr. EL, "Re: Re: Hepatic Arterial Embolization", UCLA Medicine Online.
Available Web Site: http://www.meds.com/archive/mol-cancer/1996/msg00128.html.
Burczak, et al., "Long-term in vivo performance and biocompatibility of poly (vinyl alcohol) hydrogel macrocapsules for hybrid-type artificial pancreas", Biomaterials, vol. 17, No. 24, pp. 2351-2356, 1996, abs: http://www.ncbi.nlm.nih.gov/entrez/query.fcgi?cmd=retrieve&db=PubMed&list_uids=89824..., pp. 1, 2002.
Burczak, et al., "Polymeric materials for biomedical purposes obtained by radiation methods. V. hybrid artificial pancreas", Polim Med, vol. 24, No. 1-2, pp. 45-55, 1994, abs: http://www.ncbi.nlm.nih.gov/entrez/query.fcgi?cmd=retrieve&db=PubMed&list_uids=7915..., pp. 1, 2002.
Capozza et al., "Endoscopic treatment of vesico-ureteric reflux and urinary incontinence: technical problems in the paediatric patient," British Journal of Urology, 75(4):538-542 (Apr. 1995).
Carroll, B.A. et al., "Gelatin Encapsulated Nitrogen Microbubbles as Ultrasonic Contrast Agents", Journal of Clinical and Laboratory Research, vol. 15, No. 1, pp. 260-266, Feb. 1980.
Carroll, B.A. et al., "Microbubbles as Ultrasonic Contrast Agents", Investigative Radiology, vol. 14, No. 3, p. 374, Supplement to May-Jun. 1979.
Carstensen, E.L. et al., "Determination of the Acoustic Properties of Blood and its Components", Journal of Acoustical Society of America, vol. 25, No. 2, pp. 286-289, Mar. 1953.
Choe, et al., "An experimental study of embolic effect according to infusion rate and concentration of suspension in transarterial particulate embolization", Invest Radiol, vol. 32, No. 5, pp. 260-270, 1997, abs: http://www.ncbi.nlm.nih.gov/entrez/query.fcgi?cmd=retrieve&db=PubMed&list_uids=9140745&dopt+Abs..., pp. 1, 2002.
Chuang et al., "Experimental Canine Hepatic Artery Embolization with Polyvinyl Alcohol Foam Particles", Departments of Diagnostic Radiology and Veterinary Medicine, The University of Texas, M.D. Anderson Hospital and Tumor Institute at Houston, Texas, pp. 21-25, Oct. 1982.
Cirkel, U. et al., "Experience with Leuprorelin Acetate Depot in the Treatment of Fibroids: A German Multicentre Study", Clinical Therapeutics, vol. 14, Suppl. A, 1992.
Clarian Health Methodist—Indiana Lions Gamma Knife Center, "Arteriovenous Malformation".
Available Web Site: http://www.clarian.com/tyhealth/gammaknife/cond_arter.asp.
Colombo M, "Treatment of Hepatocellular Carcinoma", University of Milan, Inst Internal Med, Irccs Maggiore Res Unit Liver, Canc, Firc, Via Pace 9 1-20122 Milan, Italy.
Source: Journal of Viral Hepatitis, 1997;4:125-130.
Available Web Site: http://home.texoma.net/~moreland/stats/hcc-9.html.
Concentric Medical, Inc.—Product Information (3 pages), 2002.
Cruise et al., "In Vitro and In Vivo Characterization of a Hydrogel-Based Aneurysm Embolization System," Society for Biomaterials 28th Annual Meeting Transactions, p. 203 (2002).
de Gast, A.N. et al., "Transforming Growth Factor β-coated Platinum Coils for Endovascular Treatment of Aneurysms: An Animal Study", Neurosurgery, vol. 49, No. 3, pp. 690-696, Sep. 2001.
Deasy, P. B., "Microencapsulation and Related Drug Processes", New York, NY, Marcel Dekker, Inc., 345 pages, 1984 (Table of Contents only).
Derdeyn, et al., "Collagen-coated acrylic microspheres for embolotherapy: in vivo and in vitro characteristics", American Journal of Neuroradiology, vol. 18, No. 4, pp. 647-653, 1997, abs: http://www.ncbi.nlm.nih.gov/entrez/query.fcgi?cmd=retrieve&db=PubMed&list_uids=9127025&dopt=Abs..., pp. 1, 2002.
Derdeyn, et al., "Polyvinyl alcohol particle size and suspension characteristics", American Journal of Neuroradiology, vol. 16, pp. 1335-1343, 1995.
DiLuccio et al., "Sustained-Release Oral Delivery of Theophylline by Use of Polyvinyl Alcohol and Polyvinyl Alcohol-Methyl Acrylate Polymers", Journal of Pharmaceutical Sciences, Jan. 1994, vol. 83, No. 1, pp. 104-106.
Duckwiler et al., "Catheters, embolic agents spark neurointervention," Diagnostic Imaging, 16(5):66-72 (May 1994).
Ersek et al., "Bioplastique: A New Textured Copolymer Microparticle Promises Permanence in Soft-Tissue Augmentation," Plastic and Reconstructive Surgery, 87(4):693-702 (Apr. 1991).
Eskridge, "Interventional Neuroradiology," Radiology, 172:991-1006 (Nov. 1989).
Feldman, L. et al., "Transcatheter Vessel Occlusion: Angiographic Results Versus Clinical Success", Radiology, vol. 147, pp. 1-5, Apr. 1983.
Ferrofluids, Physical Properties and Applications.
Ferrofluidics Corp., Nashua, NH, 5 pages, 1986.
FeRx Incorporated, FERX Profile.
http://www.biotechshares.com/FERX.htm, 4 pages (Retrieved from the internet on Jun. 26, 2003).
Fritzsch, T. et al., "SH U 508, A Transpulmonary Echocontrast Agent", Investigative Radiology, vol. 25, Supplement 1, pp. S160-S161, Sep. 1990.
Fujimoto, S. et al., "Biodegradable Mitomycin C Microspheres Given Intra-Arterially for Inoperable Hepatic Cancer", Cancer, vol. 56, pp. 2404-2410, 1985.
Gander, et al., "Effect of polymeric network structure on drug release from cross-linked poly(vinyl alcohol) micromatrices", Pharm Res, vol. 6, No. 7, pp. 578-584, 1989, abs: http://www.ncbi.nlm.nih.gov/entrez/query.fcgi?cmd=retrieve&db=PubMed&list_uids=25080..., pp. 1, 2002.
Germano, et al., "Histopathological follow-up study of 66 cerebral arteriovenous malformations after therapeutic embolization with polyvinyl alcohol", J Neurosurg, vol. 76, No. 4, pp. 607-614, 1992, abs: http://www.ncbi.nlm.nih.gov/entrez/query.fcgi?cmd=retrieve&db=PubMed&list_uids=15452..., pp. 1, 2002.
Geschwind et al., "Chemoembolization of Liver Tumor in a Rabbit Model: Assessment of Tumor Cell Death with Diffusion-Weighted MR Imaging and Histologic Analysis", Journal of Vascular and Interventional Radiology, Dec. 2000, vol. 11, No. 10, pp. 1244-1255.
Gilbert, W.M. et al., "Angiographic Embolization in the Management of Hemorrhagic Complications of Pregnancy", American Journal of Obstetrics and Gynecology, vol. 166, No. 2, pp. 493-497, Feb. 1992.
Gohel, et al., "Formulation design and optimization of modified-release microspheres of diclofenac sodium", Drug Dev Ind Pharm, vol. 25, No. 2, pp. 247-251, 1999, abs: http://www.ncbi.nlm.nih.gov/entrez/query.fcgi?cmd=retrieve&db=PubMed&list_uids=10065360&dop=A..., pp. 1, 2002.
Goldberg, B.B., "Ultrasonic Cholangiography", Radiology, vol. 118, pp. 401-404, Feb. 1976.
Goodwin, et al., "Overview of embolic agents and their indications", Eleventh Annual International Symposium on Endovascular Therapy, pp. 303-306, 1999.
Goodwin, et al., "Preliminary experience with uterine artery embolization for uterine fibroids", Journal of Vascular and Interventional Radiology, vol. 8, No. 4, pp. 517-526, 1997.

Gramiak et al., "Echocardiography of the Aortic Root," Investigative Radiology, 3(5):356-366 (Sep.-Oct. 1968).

Gramiak, R. et al., "Ultrasound Cardiography: Contrast Studies in Anatomy and Function", Radiology, vol. 92, No. 5, pp. 939-948, Apr. 1969.

Grandfils, et al., "Preparation of poly (D,L) lactide microspheres by emulsion solvent evaporation, and their clinical implications as a convenient embolic material", J Biomed Mater Res, vol. 26, No. 4, pp. 467-479, 1992, abs: http://www.ncbi.nlm.nih.gov/entrez/query.fcgi?cmd=retrieve&db=PubMed&list_uids=1601900&dopt=Abs..., pp. 1, 2002.

Greenwood, L.H. et al., "Obstetric and Nonmalignant Gynecologic Bleeding: Treatment with Angiographic Embolization", Radiology, vol. 164, No. 1, pp. 155-159, Jul. 1987.

Gupta et al., "Plasma-induced graft polymerization of acrylic acid onto poly(ethylene terephthalate) films: characterization and human smooth muscle cell growth on grafted films," Biomaterials, 23:863-871 (2002).

Halstenberg et al., "Biologically Engineered Protein-graft-Poly(ethylene glycol) Hydrogels: A Cell Adhesive and Plasmin-Degradable Biosynthetic Material for Tissue Repair," Biomacromolecules, 3(4):710-723 (2002).

Hamada, et al., "Embolization with cellulose porous beads, II: Clinical Trial", abs: http://www.ajnr.org/content/abstract/17/10/1901?ijkey=R.a2vRMiet1Xw, pp. 1-2, 2002.

Hirano et al., "Transcutaneous Intrafold Injection for Unilateral Vocal Fold Paralysis: Functional Results," Ann. Otol. Rhinol Laryngol., 99(8):598-604 (Aug. 1990).

Horak, et al., "Hydrogels in endovascular embolization. I. Spherical particles of poly (2-hydroxyethyl methacrylate) and their medicobiological properties", Biomaterials, vol. 6, 1985.

Horak, et al., "Hydrogels in endovascular embolization. II. Clinical use of spherical particles", Biomaterials, vol. 7, 1986.

Huang et al., "Hydrophilic-hydrophobic biodegradable polymers: release characteristics of hydrogen-bonded, ring-containing polymer matrices," Biomaterials, 15(15):1243-1247 (1994).

Huang, et al., "Percutaneous endovascular embolization of intracerebral arteriovenous malformations. Experience in 72 cases", Chin Med J, vol. 108, No. 6, pp. 413-419, 1995.

International Search Report for International Application No. PCT/US01/06981 (2 pages).

Jack, et al., "Radiolabeled polyvinyl alcohol particles: a potential agent to monitor embolization procedures", Int J Rad Appl Instrum B, vol. 13, No. 3, pp. 235-243, 1986.

Jiaqi, Y. et al., "A New Embolic Material: Super Absorbent Polymer (SAP) Microsphere and Its Embolic Effects," Nippon Acta Radiologica 1996 (56): 19-24.

Jones, S.K. et al., "Experimental Examination of a Targeted Hyperthermia System Using Inductively Heated Ferromagnetic Microspheres in Rabbit Kidney", Phys. Med. Biol., vol. 46, No. 2, pp. 385-398, Feb. 2001, www.iop.org/Journals/pb.

Joy C, et al., 1991, "Use of Preoperative Embolization in the Treatment of Vascular Metastatic Lesions of the Spine". Available Web Site: http://www.aaos.org/wordhtml/anmeet91/scipro/ppr472.htm.

Jung et al., "Sulfobutylated poly(vinyl alcohol)-graft-poly(lactide-co-glycolide)s facilitate the preparation of small negatively charged biodegradable nanospheres," Journal of Controlled Release, 67:157-169 (2000).

Kai, et al., "The utility of the microcrystalline cellulose sphere as a particulate embolic agent: an experimental study", American Journal of Radiology, vol. 21, No. 6, pp. 1160-1163, 2000, or http://www.ajnr.org/cgi/content/full/21/6/1160, pp. 1-7, 2002.

Kallmes, D.F. et al., "In Vitro Proliferation and Adhesion of Basic Fibroblast Growth Factor-producing Fibroblasts on Platinum Coils", Radiology, vol. 206, No. 1, pp. 237-243, Jan. 1998.

Kan, et al., "In vivo microscopy of the liver after injection of lipiodol into the hepatic artery and portal vein in the rat", Acta Radiologica, vol. 30, pp. 419-425, 1989.

Kerber et al., "Polyvinyl Alcohol Foam: Prepackaged Emboli for Therapeutic Embolization", American Journal Roentgenol, Jun. 1978, vol. 130, pp. 1193-1194.

Kerber, "Flow-Controlled Therapeutic Embolization: A Physiologic and Safe Technique", AJR, Mar. 1980, vol. 134, pp. 557-561.

Kerber, C., "Balloon Catheter with a Calibrated Leak", Radiology, vol. 120, pp. 547-550, Sep. 1976.

Khankan et al., "Embolic Effects of Superabsorbent Polymer Microspheres in Rabbit Renal Model: Comparison with Tris-acryl Gelatin Microspheres and Polyvinyl Alcohol," Radiation Medicine, 22(6):384-390 (2004).

Kim et al., "Hollow Silica Spheres of Controlled Size and Porosity by Sol-Gel Processing," J. Am. Ceram. Soc., 74(8):1987-1992 (Aug. 1991).

Kim et al., "Poly(vinyl alcohol) beads with core-shell structure for drug delivery," Cosmetic and Pharmaceutical Applications of Polymers, Plenum Press, New York, pp. 209-214 (1991).

Kim et al., "Suspension polymerized poly(vinyl alcohol) beads for drug delivery," Polymeric Materials: Science and Engineering, Proceedings of the ACS Division of Polymeric Materials: Science and Engineering, 63:64-67 (1990).

Kim, et al., "Composite poly(vinyl alcohol) beads for controlled drug delivery", Pharm Res, vol. 9. No. 1, pp. 10-16, 1992.

Kochan, J.P. et al., "Interventional Neuroradiology: Current Practices and Techniques at Temple University Hospital," http://www.temple.edu/radiology/stroke.html, 5 pages.

Krinick et al., "A polymeric drug delivery system for the simultaneous delivery of drugs activatable by enzymes and/or light," J. Biomater. Sci. Polymer Edn, 5(4):303-324 (1994).

Kuhn, R. et al., "Embolic Occlusion of the Blood Supply to Uterine Myomas: Report of 2 Cases", Aust. NZ. J. Obstet. Gynaecol., vol. 39, No. 1, pp. 120-122, Feb. 1999.

Kurata, et al., "Preoperative embolization for meningiomas using PVA particles", No Shinkei Geka, vol. 20, No. 4, pp. 367-373, 1992.

Kurbatova, G.T. et al., "Magnetically-guided Anesthetics Based on Highly Dispersed Iron Powders Coated by Polyacrylamide", Biofizika, vol. 47, No. 2, pp. 331-337, Mar.-Apr. 2002.

Kurosaki et al., "Evaluation of PVA-Gel Spheres as GI-Transit Time Controlling Oral Drug Delivery System", Proceedings of the 19th International Symposium on Controlled Release of Bioactive Materials, Jul. 26-31, 1992, Orlando, Florida, pp. 273-274.

Kusano, et al., "Low-dose particulate polyvinylalcohol embolization in massive small artery intenstinal hemorrahage. Experimental and clinical results", Invest Radiol, vol. 22, No. 5, pp. 388-392, 1987.

Labarre et al., "Complement activation by substituted polyacrylamide hydrogels for embolisation and implantation", Biomaterials, vol. 23, pp. 2319-2327, 2002.

Lammer, et al., "Transcatheteral embolization with polyvinyl alcohol—technic and experimental studies", Rontgenblatter, vol. 36, No. 1, pp. 10-14, 1983.

Latchaw et al., "Polyvinyl Foam Embolization of Vascular and Neoplastic Lesions of the Head, Neck, and Spine", Radiology, Jun. 1979, vol. 131, pp. 669-679.

Laurent, "Materials and biomaterials for interventional radiology," Biomed. & Pharmacother., 52:76-88 (1998).

Lemperle et al., "PMMA Microspheres for Intradermal Implantation: Part I. Animal Research," Annals of Plastic Surgery, 26(1):56-63 (Jan. 1991).

Lendlein, A. et al., "Biodegradable, Elastic Shape-Memory Polymers for Potential Biomedical Applications", Science, vol. 296, pp. 1673-1676, May 31, 2002.

Leung et al., "Determinants of Postembolization Syndrome after Hepatic Chemoembolization", Journal of Vascular and Interventional Radiology, Mar. 2001, vol. 12, No. 3, pp. 320-326.

Leventon, William, "Hemocompatible Coatings for Blood-Contacting Devices", Medical Device & Diagnostic Industry: Coating Technologies—New Methods to Ensure Blood Compatibility, vol. 25, No. 8, pp. 62-67, Aug. 2003.

Levy et al., "Transcatheter Uterine Artery Embolization for the Treatment of Symptomatic Uterine Fibroid Tumors," Journal of Women's Imaging, 2(4):168-175 (2000).

Lipman, "Uterine artery embolization for the treatment of symptomatic uterine fibroids: A review," Applied Radiology, 29(7):15-20 (Jul. 2000).

Lowery, C.L. et al., "Screening Tests for Intrauterine Growth Retardation: A Comparison of Umbilical Artery Doppler to Real-Time Ultrasound", Echocardiography, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", Journal of Clinical Ultrasound, vol. 3, No. 1, pp. 5-16, Mar. 1975.

Markoff, et al., "Uterine arteriovenous malformation successfully embolized with a liquid polymer, isobutyl 2-cyanoacrylate", pp. 659-660, 1999.

Markus, H.S., "Experimental Aspects of High-Intensity Transient Signals in the Detection of Emboli," J Clin Ultrasound 23:81-87 (1995).

Maruhashi, "Modified Polyvinyl Alcohols I and II," Polyvinyl Alcohol—Developments, John Wiley & Sons, Chichester, England, pp. 160-161 and pp. 186-191 (1992).

Marx, W. F. et al., "Endovascular Treatment of Experimental Aneurysms by Use of Biologically Modified Embolic Devices: Coil-mediated Intraaneurysmal Delivery of Fibroblast Tissue Allografts", AJNR. Am. J. Neuroradiol., vol. 22, pp. 323-333, Feb. 2001.

Mather, P.T., Research Group Homepage, Basic Goals and Methods, http://www.ims.uconn.edu/~mather, 4 pages.

Matsumaru, et al., "Embolic materials for endovascular treatment of cerebral lesions", J Biomater Sci Polym Ed, vol. 8, No. 7, pp. 555-569, 1997.

Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", Neurosurgery, vol. 53, No. 2, pp. 402-408, Aug. 2003.

Matsumoto, Y. et al., "Room-Temperature Ferromagnetism in Transparent Transition Metal-Doped Titanium Dioxide", Science, vol. 291, pp. 854-856, Feb. 2, 2001.

Mavligit, G. et al., "Gastrointestinal Leiomyosarcoma Metastatic to the Liver, " Cancer, vol. 75, No. 8, Apr. 15, 1995, pp. 2083-2088.

McIvor, J. et al., "Pregnancy After Uterine Artery Embolization to Control Haemorrhage from Gestational Trophoblastic Tumour", British Journal of Radiology, vol. 69, No. 823, pp. 624-629, Jul. 1996.

MerocelXL Sponge with Hytrol, http://www.xomed.com/newproducts/merocelxl/merocelx1_earwick.asp, 3 pages, 2001.

Mid-America Interventional Radiological Society, "New Treatment for Uterine Fibroids Avoids Surgery" Available Web Site: http://www.mirs.org/fibroids.htm.

Moroz, P. et al., "Arterial Embolization Hyperthermia in Porcine Renal Tissue", Journal of Surgical Research, vol. 105, No. 2, pp. 209-214, Jun. 15, 2002.

Moroz, P. et al., "Hepatic Clearance of Arterially Infused Ferromagnetic Particles", Int. J. Hyperthermia, vol. 19, No. 1, pp. 23-24, Feb. 2003, http://www.tandf.co.uk/journals.

Nakabayashi, et al., "Evaluation of particulate embolic materials with MR imaging, scanning electron microscopy, and phase-contrast microscopy", American Journal of Neuroradiology, vol. 18, No. 3, pp. 485-491, 1997.

Nakstad, et al., "Embolization of intracranial arteriovenous malformations and fistulas with polyvinyl alcohol particles nad platinum fibre coils", Neuroradiology, vol. 34, No. 4, pp. 348-351, 1992.

Namiki, "Application of Teflon Paste for Urinary Incontinence—Report of 2 Cases," Uro. Int., 39:280-282 (1984).

Nash, et al., "Modifications of polystyrenic matrices for the purification of proteins. II. Effect of the degree of glutaraldehyde-poly(vinyl alcohol) crosslinking on various dye ligand chromatography systems", J Chromatogr A, vol. 776, No. 1, pp. 55-63, 1997.

Nikishin LF et al., 1999, "Interventional radiology in diffuse toxic goiter", European Congress of Radiology—ECR 1999.

Ophir, et al., "Ultrasonic backscatter from contrast producing collagen microspheres", Ultrasonic Imaging, vol. 2, pp. 67-77, 1980.

Oregon Health Sciences University, "Fibroid Embolization" Available Web Site: http://www.uhmc.edu/dotter-fibroid.

Orienti et al., "Crosslinked Polyvinylalcohol Hydrogels as Vehicles for Hydrophilic Drugs," Arch. Pharm. Pharm. Med. Chem., 333:421-424 (2000).

Orsini, L. F. et al., "Pelvic Organs in Premenarcheal Girls: Real-Time Ultrasonography", Radiology, vol. 153, No. 1, pp. 113-116, Oct. 1984.

Parker, et al., "A particulate contrast agent with potential for ultrasound imaging of liver", Ultrasound in Medicine and Biology, vol. 13, No. 9, pp. 555-566, 1987.

Pedley et al., "Hydrogels in Biomedical Applications," British Polymer Journal, 12:99-110 (Sep. 1980).

Pesant A.C. et al., 1997, "Dural fistulas involving the cavernous sinus: Treatment by embolization—7 cases", European Congress of Radiology—ECR 1997 Available Web Site: http://www.ecr.org/conferences/ecr1997/sciprg/abs/9703088p.htm.

Phillips, D. R. et al., "Experience with Laparoscopic Leiomyoma Coagulation and Concomitant Operative Hysteroscopy", J. Am. Assoc. Gynecol. Laparosc, vol. 4, No. 4, pp. 425-533, Aug. 1997.

Physicians' Desk Reference Family Guide to Women's Health, "Chapter 7—Common Disorders of the Reproductive System" Available Web Site: http://www.healthsquare.com/pdrfg/wh/chapters/wh1ch01.htm.

Pistel et al., "Brush-like branched biodegradable polyesters, part III Protein release from microspheres of poly(vinyl alcohol)-graft-poly(D,L-lactic-co-glycolic acid)," Journal of Controlled Release, 73:7-20 (2001).

Politano et al., "Periurethral Teflon Injection for Urinary Incontinence," The Journal of Urology, 111:180-183 (1974).

Poppe, W. et al., "Pregnancy after Transcatheter Embolization of a Uterine Arteriovenous Malformation", Am. J. Obstet. Gynecol., vol. 156, No. 5, pp. 1179-1180, May 1987.

Pritchard, et al., "Poly(Vinyl Alcohol): Basic Properties and Uses", London, England: Gordon and Breach Science Publishers.

Progelhof et al., "Table 4.21. Properties of electrical insulating films (101)," Polymer Engineering Principles: Properties, Processes, and Tests for Design, Hanser Publishers, Munich, p. 383 (1993).

Pryor J and Berenstein A., "Epistaxis (Nose-bleeds)" Available Web Site: http://www.wehealny.org/inn/Radiology/nosebleeds.html.

Purdy, et al., "Arteriovenous malformations of the brain: choosing embolic materials to enhance safety and ease of excision", J Neurosurg, vol. 77, No. 2, pp. 217-222, 1992.

PVA Plus, AngioDynamics® Inc., "Reliable PVA Foam Formulated for Consistency and Controlled Delivery—Embolization Particles Ordering Information," www.angiodynamics.com, 2 pages (Aug. 2002).

Quisling, et al., "Histopathology analysis of intraarterial polyvinyl alcohol microemboli in rat cerebral cortex", American Journal of Neuroradiology, vol. 5, pp. 101-104, 1984.

Rajan et al., "Sarcomas Metastatic to the Liver: Response and Survial after Cisplatin, Doxorubicin, Mitomycin-C, Ethiodol, and Polyvinyl Alcohol Chemoembolization", Journal of Vascular and Interventional Radiology, Feb. 2001, vol. 12, No. 2, pp. 187-193.

Ramos, et al., "Tumor vascular signals in renal masses: detection with Doppler US", Radiology, vol. 168, No. 3, pp. 633-637, 1988.

Ravina, J.H. et al., "Advantage of Pre-Operative Embolization of Fibroids: About a Multicentric Set of 31 Cases", Contracept. Fertil. Sex., vol. 23, No. 1, pp. 45-49, Jan. 1995 (abstract).

Ravina, J.H. et al., "Arterial Embolisation to Treat Uterine Myomata", Lancet, vol. 346, pp. 671-674, Sep. 9, 1995.

Ravina, J.H. et al., "Interest of Particulate Arterial Embolization in the Treatment of Some Uterine Myoma", Bull. Acad. Natle. Med., vol. 181, No. 2, pp. 233-246, Feb. 4, 1997 (Summary).

Repa, I. et al., "Mortalities Associated with Use of a Commercial Suspension of Polyvinyl Alcohol", Radiology 1989; 170:395-399.

Rhine et al., "Polymers for Sustained Macromolecule Release: Procedures to Fabricate Reproducible Delivery Systems and Control Release Kinetics," Journal of Pharmaceutical Sciences, 69(3):265-270 (Mar. 1980).

Rump, A. et al., "Pharmacokinetics of Intraarterial Mitomycin C in the Chemoembolisation Treatment of Liver Metastases", Gen. Pharmac. vol. 27, No. 4, pp. 669-671, 1996.

Schetky, "Shape-Memory Alloys," Encyclopedia of Chemical Technology, Third Edition, vol. 20, John Wiley & Sons, New York, pp. 726-736 (1982).

Schlief, R. et al., "Enhanced Color Doppler Echocardiography of the Left Heart After Intravenous Injection of a New Saccharide Based Agent in Humans", Circulation, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", Echocardiography, vol. 7, No. 1, pp. 61-64, Jan. 1990.

Schwarz, K.Q., "The Acoustic Filter: An Ultrasonic Blood Filter for the Heart-Lung Machine," J Thoracic and Cardiovascular Surgery 104(6):1647-1653 (1992).

Shafik, "Intraesophageal Polytef injection for the treatment of reflux esophagitis," Surg. Endosc., 10:329-331 (1996).

Shafik, A., "Intraesophageal Polytef injection for the treatment of reflux esophagitis", Department of Surgery and Experimental Research, Faculty of Medicine, Cairo University, Cairo, Egypt, pp. 1-2, Received: Jun. 22, 1994; Accepted: Oct. 15, 1994 http://www.ahmedshafik.org/Group-D/d016.htm.

Shape Shifters, http://www.sciam.com/tehbiz/0501scicit6.html, 3 pages, 2001.

Shung, K.K. et al., "Scattering of Ultrasound by Blood", IEEE Transactions on Biomedical Engineering, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", Journal of Acoustical Society of America, vol. 53, No. 4, pp. 1351-1355, Apr. 1973.

SIR-Spheres (Yttrium-90 Microspheres), pp. 1-12.

SIR-Spheres, Radioactive Implant (Yttrium-90 Microspheres), Sirex Medical, Inc., San Diego, CA, Nov. 6, 2000, pp. 1-15.

Sirtex Medical Limited—Product Description http://www.sirtex.com/?p=72, 3 pages (Retrieved from the internet on May 27, 2003).

Sirtex Medical Limited—Targeted Radiotherapy with SIR-Spheres http://www.sirtex.com/?p=57, 2 pages (Retrieved from the internet on May 27, 2003).

Siskin et al., "Pathologic Evaluation of a Spherical Polyvinyl Alcohol Embolic Agent in a Porcine Renal Model," J. Vasc. Interv. Radiol., 14:89-98 (2003).

Skotland, T. et al., "In Vitro Stability Analyses as a Model for Metabolism of Ferromagnetic Particles (Clariscan), a Contrast Agent for Magnetic Resonance Imaging", J. Pharm. Biomed. Anal., vol. 28, No. 2, pp. 323-329, Apr. 15, 2002.

Smith et al., "Evaluation of Polydimethylsiloxane as an alternative in the Endoscopic Treatment of Vesicoureteral Reflux," The Journal of Urology, 152:1221-1224 (Oct. 1994).

Smith et al., "Left Heart Opacification with Peripheral Venous Injection of a New Saccharide Echo Contrast Agent in Dogs", JACC, vol. 13, No. 7, pp. 1622-1628, Jun. 1989.

Soppimath et al., "Controlled release of antihypertensive drug from the interpenetrating network poly(vinyl alcohol)-guar gum hydrogel microspheres," J. Biomater. Sci. Polymer Edn, 11(1):27-43 (2000).

Spickler, et al., "The MR appearance of endovascular embolic agents in vitro with clinical correlation", Comput Med Imaging Graph, vol. 14, No. 6, pp. 415-423, 1990.

Spies JB, "Georgetown University Medical Center. Uterine Fibroid Embolization (UFE). An alternative to surgery for patients with uterine fibroids. Literature Review." Available Web Site: http://www.dml.georgetown.edu/fibroids.

EMBOLIZATION

This application is a continuation (and claims the benefit of priority under 35 U.S.C. §120) of U.S. application Ser. No. 11/923,009, filed Oct. 24, 2007, which is a continuation (and claims the benefit of priority under 35 U.S.C. §120) of U.S. application Ser. No. 10/858,253, filed Jun. 1, 2004.

TECHNICAL FIELD

This invention relates to embolization, as well as related particles and methods.

BACKGROUND

Therapeutic vascular occlusions (embolizations) are used to prevent or treat pathological conditions in situ. Compositions including embolic particles are used for occluding vessels in a variety of medical applications. Delivery of embolic particles through a catheter is dependent on size uniformity, density and compressibility of the embolic particles.

SUMMARY

In one aspect, the invention features a method of making particles. The method includes combining a plurality of streams (e.g., two streams, three streams) of fluid to form drops, and forming particles from the drops. The arithmetic mean diameter of the particles is from about ten microns to about 3,000 microns.

In another aspect, the invention features a method of making particles. The method includes combining a stream that includes a polymer and a different stream that includes a gelling precursor to form drops. The method also includes forming particles from the drops.

In a further aspect, the invention features a method of making particles. The method includes forming a plurality of streams (e.g., two streams, three streams) of fluid from a plurality of orifices (e.g., two orifices, three orifices), combining the plurality of streams of fluid to form drops, and forming particles from the drops. A first orifice has a diameter of from about 50 microns to about 1000 microns (e.g., from about 50 microns to about 300 microns). A second orifice has an inner diameter of from about 50 microns to about 1000 microns (e.g., from about 300 microns to about 600 microns) and an outer diameter of from about 50 microns to about 1000 microns (e.g., from about 300 microns to about 600 microns). The outer diameter of the second orifice is different from the diameter of the first orifice.

Embodiments can include one or more of the following features.

The plurality of streams of fluid can include a first stream that includes a first material and a second stream that includes a second material.

The first material (e.g., a polymer) can form an interior region of the drops and the second material (e.g., a gelling precursor) can form a surface region of the drops.

The first material can include a polymer, such as, for example, a polyvinyl alcohol, a polyacrylic acid, a polymethacrylic acid, a poly vinyl sulfonate, a carboxymethyl cellulose, a hydroxyethyl cellulose, a substituted cellulose, a polyacrylamide, a polyethylene glycol, a polyamide, a polyurea, a polyurethane, a polyester, a polyether, a polystyrene, a polysaccharide, a polylactic acid, a polyethylene, a polymethylmethacrylate, a polycaprolactone, a polyglycolic acid, a poly(lactic-co-glycolic) acid, or a combination of two or more of these polymers.

The second material can include a gelling precursor, such as a polysaccharide (e.g., alginate).

The first material and the second material can be immiscible.

The first material and/or the second material can include a therapeutic agent.

The viscosity of the first material can be greater than the viscosity of the second material. The viscosity of the second material can be greater than the viscosity of the first material.

The first material and/or second material can be ferromagnetic, MRI-visible (visible by magnetic resonance imaging), and/or radiopaque.

The first stream and the second stream can be concentric.

The method can further include contacting the first stream with the second stream (e.g., by forming a mixture of the first and second materials).

The method can further include forming the first stream by flowing the first material through a first orifice that is defined by a nozzle.

The first material can flow through the first orifice at a rate of from about two milliliters per minute to about ten milliliters per minute.

The method can further include forming the second stream by flowing the second material through a second orifice that is defined by the nozzle.

The second material can flow through the second orifice at a rate of from about two milliliters per minute to about 20 milliliters per minute.

The first orifice can be disposed within the second orifice. For example, the first orifice and the second orifice can be concentric.

The first orifice can be disposed at a vertical distance of about one millimeter from the second orifice.

The first orifice can have a diameter of from about 50 microns to about 1000 microns (e.g., from about 50 microns to about 300 microns).

The second orifice can have an inner diameter of from about 50 microns to about 1000 microns (e.g., from about 100 microns to about 600 microns, from about 300 microns to about 600 microns), and/or an outer diameter of from about 50 microns to about 1,000 microns (e.g., from about 100 microns to about 600 microns, from about 300 microns to about 600 microns).

The difference between the outer diameter of the second orifice and the diameter of the first orifice can be at least about 50 microns (e.g., about 100 microns).

The method can further include adding a therapeutic agent to the particles.

The method can further include contacting the drops with a gelling agent to form the particles.

Forming the particles can include converting the gelling precursor from a solution into a gel. The method can further include removing at least some of the gelling precursor from the particles.

The method can further include reacting the particles with a cross-linking agent.

The method can further include removing at least some of the gelling precursor from the particles.

One or more of the particles can have a diameter of from about ten microns to about 3,000 microns. The particles can have an arithmetic mean diameter of from about ten microns to about 3,000 microns.

The interior region of the particles can be substantially free of the polymer and of the gelling precursor.

The density of the polymer in the interior region of the particles can be higher than the density of the polymer at the surface region of the particles. The density of the gelling precursor at the surface region of the particles can be higher than the density of the gelling precursor in the interior region of the particles.

The particles can contain pores. The density of pores in the interior region of the particles can be different from (e.g., greater than) the density of pores at the surface region of the particles. The average pore size in the interior region of the particles can be different from (e.g., greater than) the average pore size at the surface region of the particles.

The particles can be substantially non-porous.

Forming the drops can include exposing the plurality of streams to a periodic disturbance. The periodic disturbance can be provided by vibrating the plurality of streams.

Forming the drops can include establishing an electrostatic potential between the plurality of streams and a vessel configured to receive the drops.

Embodiments can include one or more of the following advantages.

The methods can provide for a relatively effective and/or efficient way to make particles (e.g., embolic particles), particularly particles that include more than one material. For example, different orifices can be used to introduce different materials during the process of preparing the particles. Particles including multiple materials can be desirable, for example, in embolization procedures. As an example, it can be desirable for an embolic particle to include a therapeutic agent (e.g., to treat a tumor). As another example, it can be desirable for an embolic particle to include a radiopaque material (e.g., to enhance the ability to view the particle in the body using fluoroscopy). As a further example, it can be desirable for an embolic particle to include a ferromagnetic material to enhance the ability to manipulate the position of the particle in the body using a magnetic field.

The methods can provide for a relatively effective and/or efficient way to make particles (e.g., embolic particles) of a desired size. As an example, the streams of material that flow from different orifices can be independently manipulated to provide a particle of a desired size. As another example, the viscosity of the streams can be manipulated (e.g., reduced) to form particles of a desired size (e.g., smaller particles).

The methods can, for example, be used to form hollow particles. When used, for example, in an embolization procedure, hollow particles can be loaded shortly before the procedure (e.g., immediately before the procedure), which can reduce the cost and/or complexity associated with storing embolic compositions that include, for example, a carrier solution in addition to the particles.

Features and advantages are in the description, drawings, and claims.

DETAILED DESCRIPTION

Figure 1A:
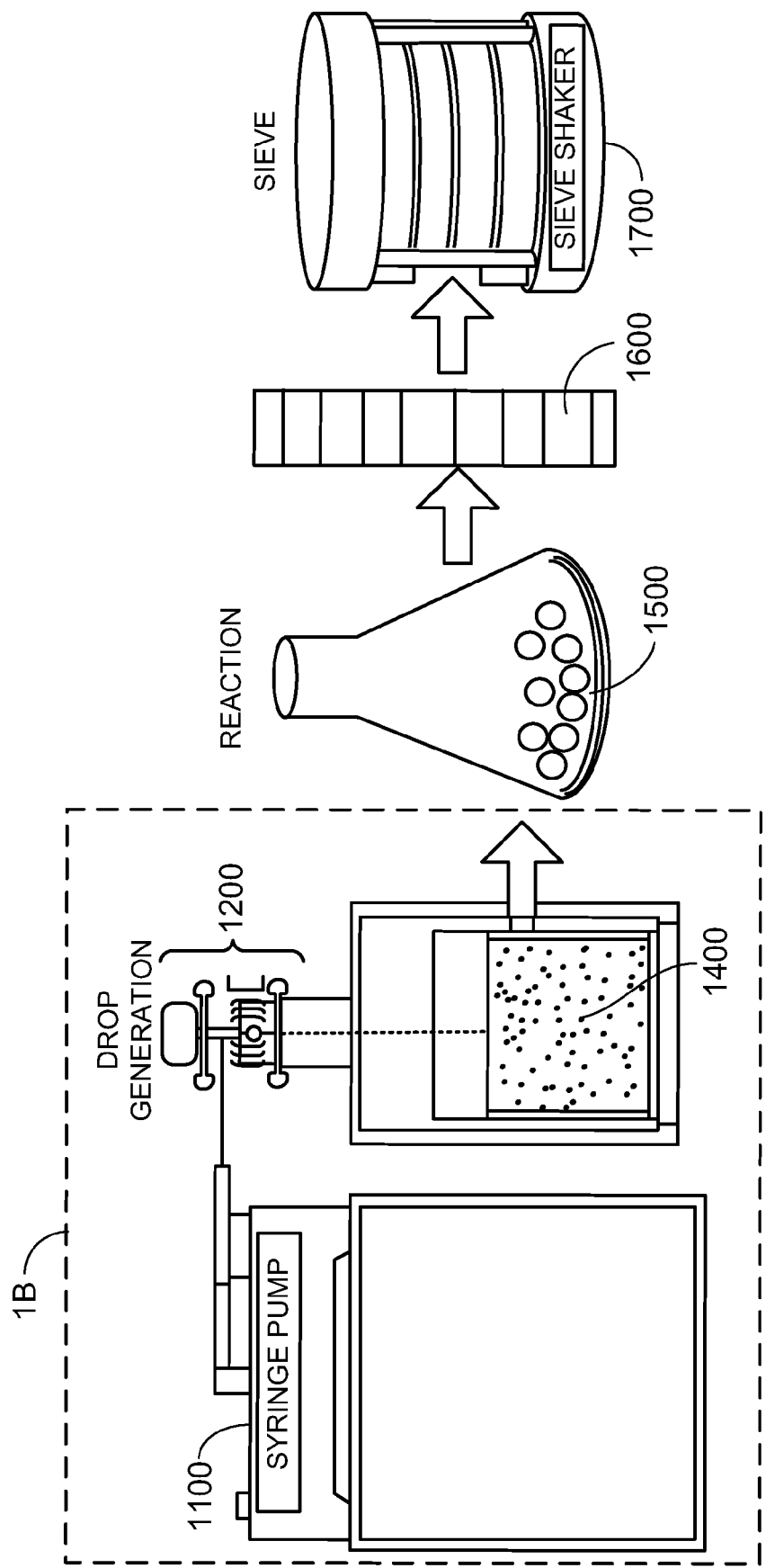
FIG. 1A is a schematic of the manufacture of an embolic composition.
Figure 1B:
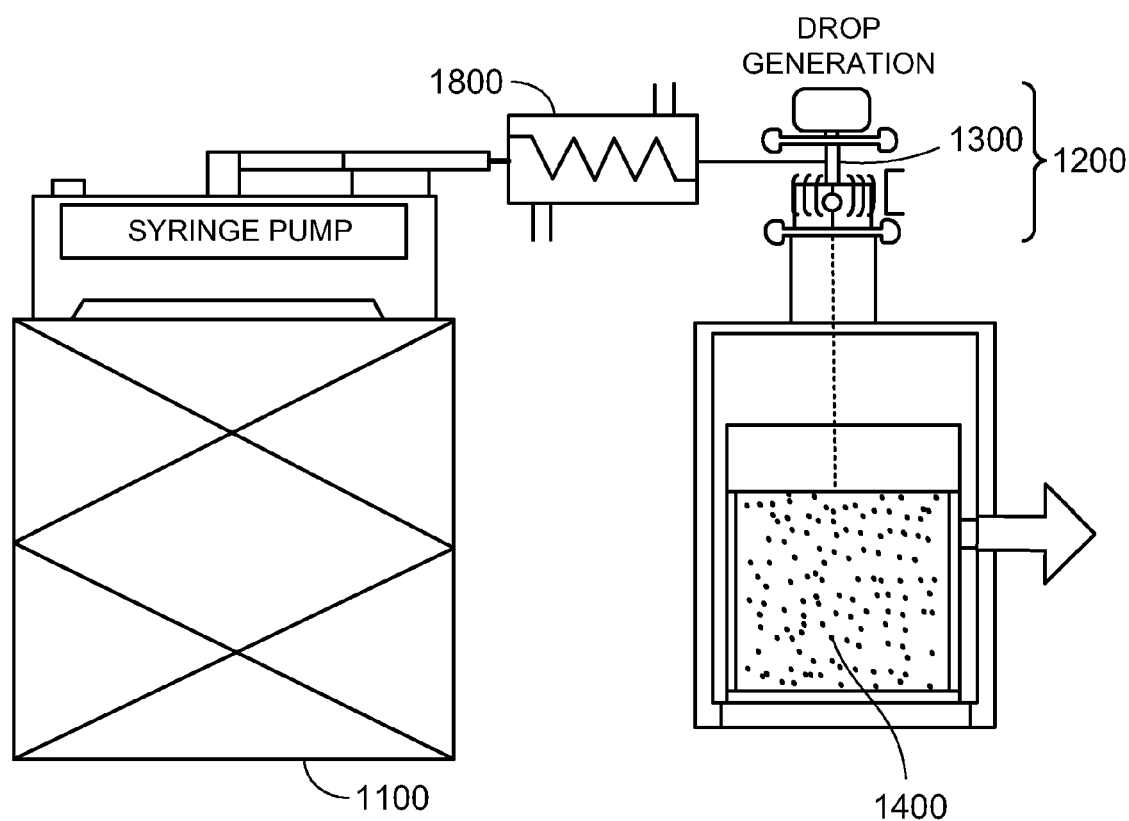
FIG. 1B is an enlarged schematic of region 1B in FIG. 1A.
Figure 2A:
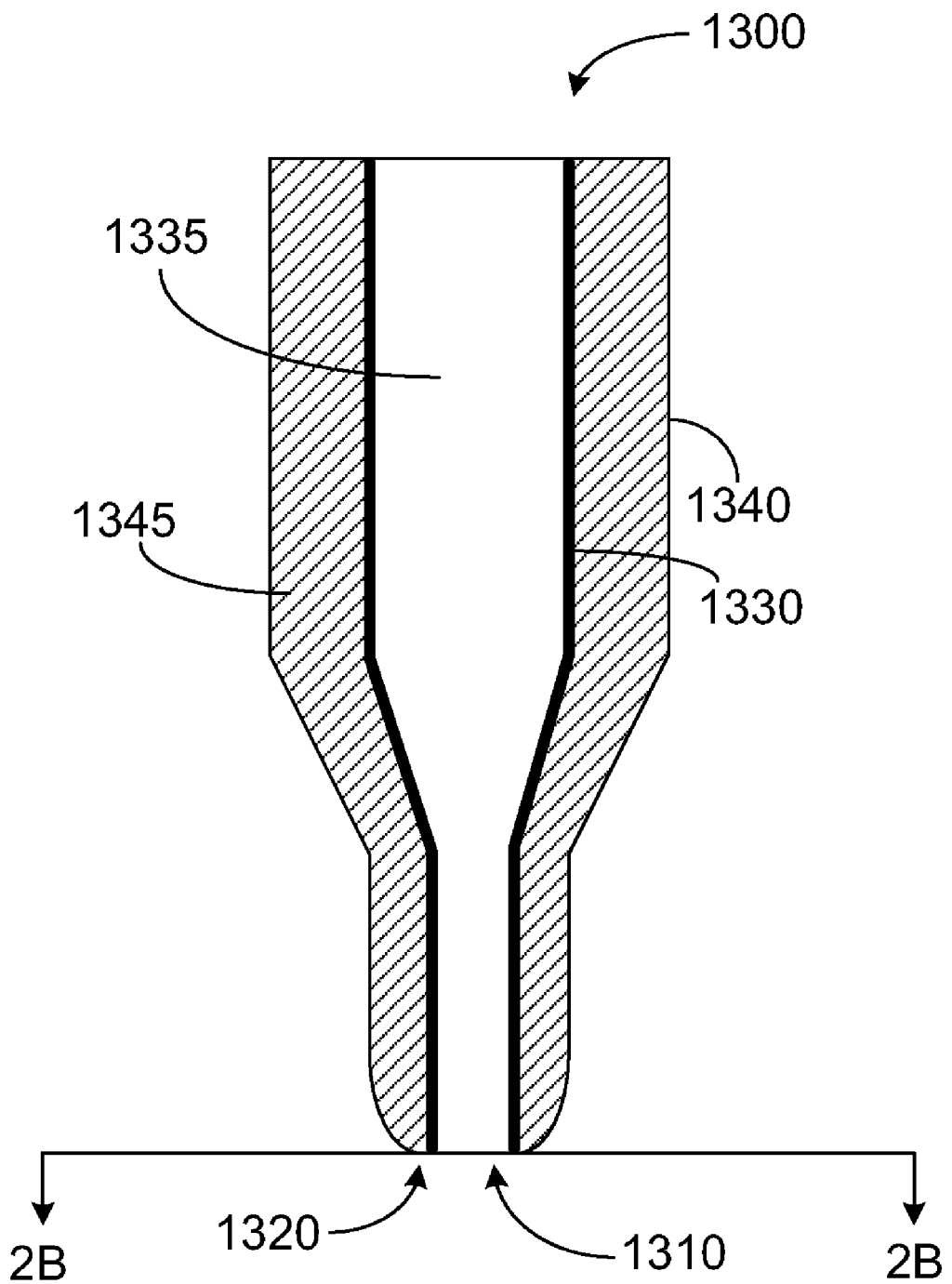
FIG. 2A is a cross-sectional view of an embodiment of an apparatus for producing particles.
Figure 2B:
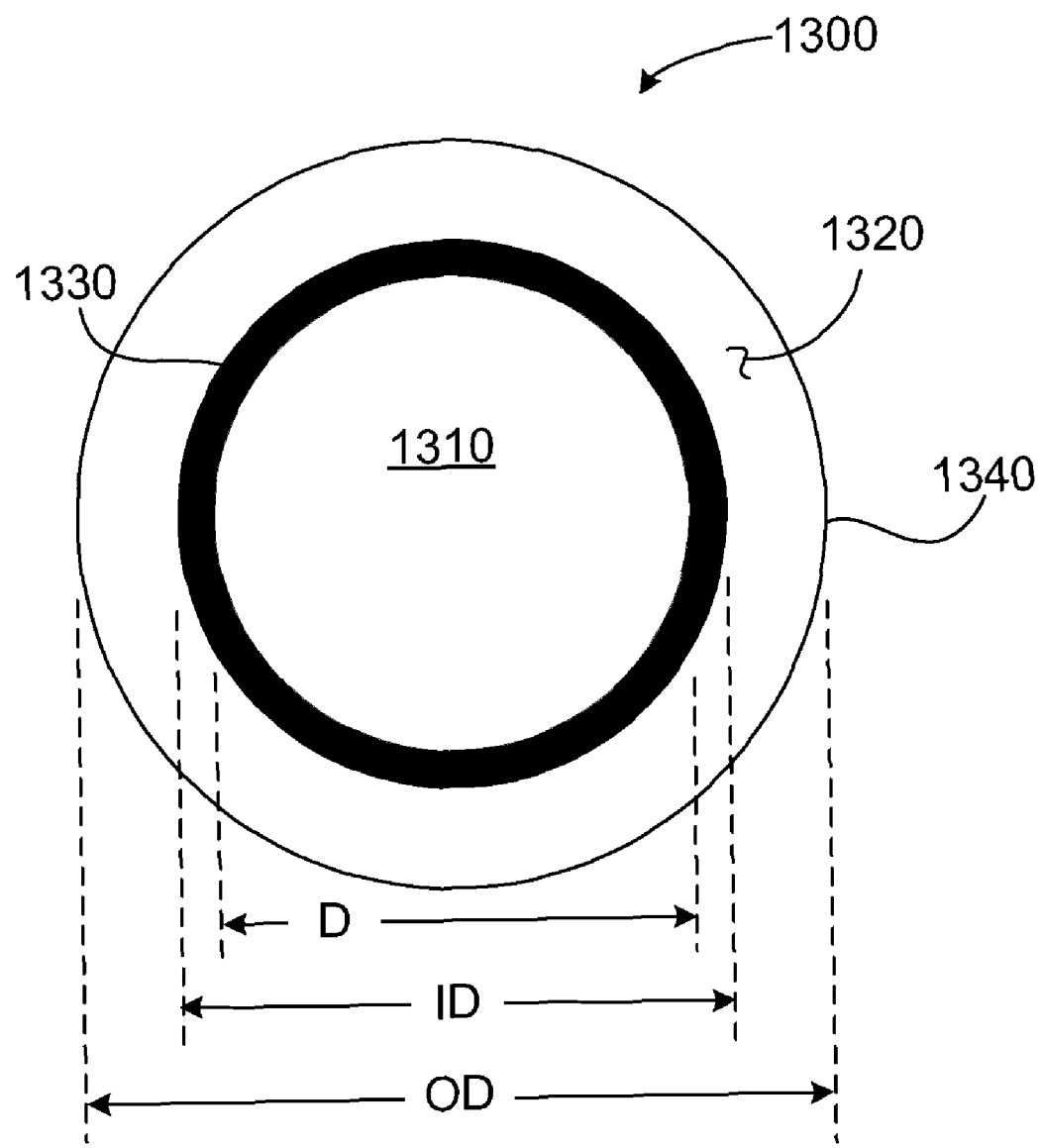
FIG. 2B is an enlarged view of the apparatus of FIG. 2A, taken along line 2B-2B.

FIGS. 1A and 1B show a system 1000 for producing particles (e.g., particles that can be used in an embolization procedure). System 1000 includes a flow controller 1100, a drop generator 1200, a gelling vessel 1400, a reactor vessel 1500, an optional gel dissolution chamber 1600, and a filter 1700. Drop generator 1200 includes a concentric nozzle 1300. As shown in FIGS. 2A and 2B, concentric nozzle 1300 includes an inner nozzle 1330 with an inner volume 1335 and an orifice 1310 having a diameter "D." Concentric nozzle 1300 also includes an outer nozzle 1340 with an inner volume 1345 (shaded in FIG. 2A) and an orifice 1320 having an inner diameter "ID" and an outer diameter "OD."

Drop generator 1200 can be, for example, the Inotech Encapsulator unit IE-50R/NS (Inotech AG, Dottikon, Switzerland), or the model NISCO Encapsulation unit VAR D (NISCO Engineering, Zurich, Switzerland). In some embodiments, concentric nozzle 1300 can be provided as an attachment to drop generator 1200. An example of a concentric nozzle attachment is the model IE-5250 attachment (available from Inotech AG).

Flow controller 1100 delivers two solutions (a polymer solution and a gelling precursor solution) to a viscosity controller 1800, which heats one or both of the solutions to achieve their respective desired viscosities prior to delivery to drop generator 1200. In certain embodiments, before being transferred to drop generator 1200, one or both of the solutions can be introduced to a high pressure pumping apparatus, such as a syringe pump (e.g., model PHD4400, Harvard Apparatus, Holliston, Mass.). Alternatively or additionally, drop generator 1200 can contain a pressure control device that applies a pressure (e.g., from about 0.5 Bar to about 1.6 Bar) to one or both of the solutions (a pressure head) to control the rates at which the solutions are transferred to drop generator 1200. Generally, the pressure applied to a given solution depends on the viscosity of the solution and/or the desired flow rate of the solution.

Figure 2C:
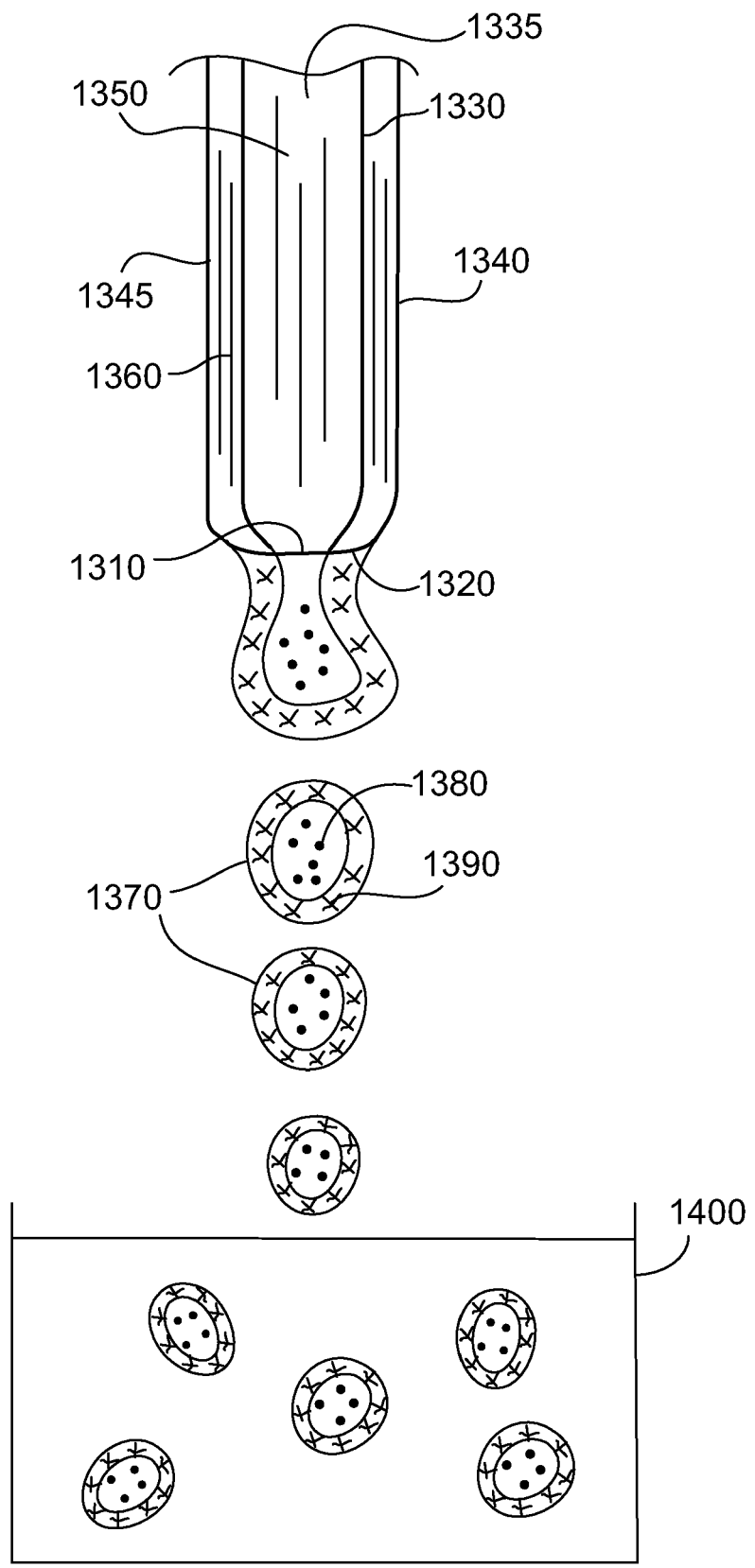
FIG. 2C is an illustration of the production of particles by the apparatus of FIGS. 2A and 2B.

As shown in FIG. 2C, after being delivered to drop generator 1200, a stream 1350 of the polymer solution passes through volume 1335 and exits inner nozzle 1330 via orifice 1310. A stream 1360 of the gelling precursor solution passes through volume 1345 and exits outer nozzle 1340 via orifice 1320. In some embodiments, stream 1350 and/or stream 1360 can have an average diameter that is about two times the outer diameter of the nozzle through which the stream exits. The streams interact as they exit the orifices. At the same time, nozzle 1300 is subjected to a periodic disturbance which results in the formation of drops 1370 having an interior region 1380 formed of the polymer and an exterior region 1390 formed of the gelling precursor. Drops 1370 fall into gelling vessel 1400, where the drops are stabilized by gel formation during which the gelling precursor is converted from a solution form to a gel form. The gel-stabilized drops are then transferred from gelling vessel 1400 to reactor vessel 1500, where the polymer in the gel-stabilized drops is reacted, forming particles. Thereafter, the particles are filtered in filter 1700 to remove debris, and are sterilized and packaged as an embolic composition including embolic particles. In some embodiments, the particles are transferred, prior to filtration, to gel dissolution chamber 1600. In gel dissolution chamber 1600, the gelling precursor (which was converted to a gel) in the particles is dissolved. After the gelling precursor is dissolved, the particles can be filtered, sterilized, and packaged, as described above.

In general, one or more of the parameters of the drop generation process can be selected to form drops of a desired size. Drop size can be controlled, for example, by controlling the diameter "D" of inner orifice 1310, the inner diameter "ID" of orifice 1320, the outer diameter "OD" of orifice 1320, the flow rate of stream 1350, the flow rate of stream 1360, the viscosity of the polymer solution, the viscosity of the gelling precursor solution, the vibration amplitude of concentric nozzle 1300, and/or the vibration frequency of concentric nozzle 1300. As an example, holding other parameters constant, increasing the diameter "D" of inner orifice 1310, increasing the inner diameter "ID" of orifice 1320, and/or increasing the outer diameter "OD" of orifice 1320 generally results in the formation of larger drops. As another example, holding other parameters constant, increasing the flow rate of stream 1350 and/or increasing the flow rate of stream 1360 generally results in larger drops. As an additional example, holding other parameters constant, reducing the vibration frequency of concentric nozzle 1300 generally results in larger drops. As a further example, holding other parameters constant, increasing the viscosity of the polymer solution and/or increasing the viscosity of the gelling precursor solution generally results in larger drops.

In general, the diameter "D" of inner orifice 1310 can be from about 50 microns to about 1,000 microns (e.g., from about 50 microns to about 300 microns, from about 100 microns to about 300 microns, from about 200 microns to about 300 microns, about 200 microns, about 300 microns). In some embodiments, diameter "D" can be about 300 microns or less (e.g., about 200 microns or less, about 150 microns or less, about 100 microns or less) and/or about 50 microns or more (e.g., about 100 microns or more, about 150 microns or more, about 200 microns or more, about 250 microns or more).

Orifice 1320 typically can have an outer diameter "OD" of from about 50 microns to about 1,000 microns (e.g., from about 100 microns to about 600 microns, from about 300 microns to about 600 microns, from about 300 microns to about 500 microns, about 500 microns, about 600 microns). In certain embodiments, orifice 1320 can have an outer diameter "OD" of about 100 microns or more (e.g., about 200 microns or more, about 300 microns or more, about 400 microns or more, about 500 microns or more) and/or about 600 microns or less (e.g., about 500 microns or less, about 400 microns or less, about 300 microns or less, about 200 microns or less).

Generally, orifice 1320 can have an inner diameter "ID" of from about 50 microns to about 1,000 microns (e.g., from about 100 microns to about 600 microns, from about 300 microns to about 600 microns, from about 300 microns to about 500 microns, from about 400 microns to about 500 microns, about 400 microns, about 500 microns). In some embodiments, orifice 1320 can have an inner diameter "ID" of about 600 microns or less (e.g., about 500 microns or less, about 400 microns or less, about 300 microns or less, about 200 microns or less) and/or about 100 microns or more (e.g., about 200 microns or more, about 300 microns or more, about 400 microns or more, about 500 microns or more).

The difference between the outer diameter "OD" of orifice 1320 and the diameter "D" of inner orifice 1310 can be at least about 50 microns (e.g., at least about 100 microns, at least about 200 microns, at least about 300 microns), and/or at most about 300 microns (e.g., at most about 200 microns, at most about 100 microns). In some embodiments, the difference between the outer diameter "OD" of orifice 1320 and the diameter "D" of inner orifice 1310 can be about 100 microns.

In general, stream 1350 of polymer solution can flow through volume 1335 of inner nozzle 1330 at a rate of from about two milliliters per minute to about ten milliliters per minute. In some embodiments, stream 1350 can flow through volume 1335 at a rate of more than about two milliliters per minute (e.g., more than about five milliliters per minute, more than about seven milliliters per minute, more than about ten milliliters per minute) and/or less than about ten milliliters per minute (e.g., less than about seven milliliters per minute, less than about five milliliters per minute, less than about two milliliters per minute).

Generally, stream 1360 of gelling precursor solution can flow through volume 1345 at a rate of from about two milliliters per minute to about 20 milliliters per minute (e.g., from about four milliliters per minute to about 20 milliliters per minute, from about five milliliters per minute to about 20 milliliters per minute). In some embodiments, stream 1360 can flow through volume 1345 at a rate of more than about five milliliters per minute (e.g., more than about seven milliliters per minute, more than about ten milliliters per minute, more than about 15 milliliters per minute) and/or less than about 20 milliliters per minute (e.g., less than about 15 milliliters per minute, less than about ten milliliters per minute, less than about seven milliliters per minute).

In some embodiments, the flow rates of streams 1350 and 1360 are about the same. For example, streams 1350 and 1360 can both flow through concentric nozzle 1300 at a rate of about five milliliters per minute.

In certain embodiments, the flow rate of stream 1350 is different from the flow rate of stream 1360. For example, stream 1350 can flow through volume 1335 at a rate of about five milliliters per minute, and stream 1360 can flow through volume 1345 at a rate of about ten milliliters per minute. In some embodiments, a variation in the flow rates of streams 1350 and 1360 through nozzle 1300 can enhance mixing between the streams at their interface.

In some embodiments, stream 1360 can begin to flow through concentric nozzle 1300 before stream 1350 begins to flow through concentric nozzle 1300. In certain embodiments, stream 1350 can begin to flow through concentric nozzle 1300 before stream 1360 begins to flow through concentric nozzle 1300. In such embodiments, mixing between the streams at the interface can be relatively low.

In some embodiments, the vibration frequency of concentric nozzle 1300 can be about 0.1 KHz or more (e.g., about 0.8 KHz or more, about 1.5 KHz or more, about 1.75 KHz or more, about 1.85 KHz or more, about 2.5 KHz or more, from about 0.1 KHz to about 0.8 KHz).

In certain embodiments, the vibration amplitude of concentric nozzle 1300 is larger than the width of the drops 1370. In some embodiments, drop generator 1200 has a variable vibration amplitude setting, such that an operator can adjust the amplitude of the concentric nozzle vibration. In such embodiments, the vibration amplitude can be set, for example, at between about 80 percent and about 100 percent of the maximum setting.

In general, the viscosity of the polymer solution can be from about ten centipoise to about 50 centipoise (e.g., about 25 centipoise). Alternatively or additionally, the viscosity of the gelling precursor solution can be from about ten centipoise to about 100 centipoise (e.g., about 50 centipoise). In some embodiments, a solution with a viscosity of about 50 centipoise can produce drops with a diameter of from about 100 microns to about 1200 microns. Typically, the viscosity of a concentric stream of two different materials can be lower than the viscosity of a mixed stream of the two different materials. Generally, a lower viscosity solution can flow through a smaller orifice than a higher viscosity solution, and thus can produce smaller drops than the higher viscosity solution.

As described above, viscosity controller 1800 can be used in the drop formation process to control the viscosity of the polymer solution and the gelling precursor solution. Viscosity controller 1800 is a heat exchanger that circulates water at a predetermined temperature about the flow tubing between the pump and drop generator 1200. The polymer solution and the gelling precursor solution flow into viscosity controller 1800, where the solutions are heated so that their viscosities are lowered to a desired level. Alternatively or additionally, vessels containing the solutions can be disposed in a heated fluid bath (e.g., a heated water bath) to heat the solutions. In some embodiments (e.g., when the system does not contain viscosity controller 1800), flow controller 1100 and/or drop generator 1200 can be placed in a temperature-controlled chamber (e.g. an oven, a heat tape wrap) to the heat polymer solution and the gelling precursor solution. In general, for a given solution, the lower the desired viscosity of the solution, the higher the temperature to which the solution is heated. For example, in some embodiments, a solution with a desired viscosity of about 100 centipoise can be heated to a temperature of about 65° C., while a solution with a desired viscosity of about 50 centipoise can be heated to a temperature of about 75° C. In certain embodiments, viscosity controller 1800 can heat the solutions to allow for flow through an orifice of a particular size. Generally, for a given solution, the smaller the size of the nozzle orifice, the higher the temperature to which the solution is heated. For example, in some embodiments, a solution that flows through an orifice with a diameter of about 200 microns can be heated to a temperature of about 65° C., while the same solution, when flowing through an orifice with a diameter of about 100 microns, can be heated to a temperature of about 75° C.

The viscosity of the polymer solution and/or the gelling precursor solution can alternatively or additionally be adjusted by changing the concentration of the polymer and/or gelling precursor in the solution. In general, as the concentration of polymer and/or gelling precursor in the solution increases, the viscosity of the solution increases. If, for example, the desired viscosity of a polyvinyl alcohol solution is about 25 centipoise, then the solution can be prepared to have a concentration of about eight percent polyvinyl alcohol. If, for example, the desired viscosity of an alginate solution is about 50 centipoise, then the solution can be prepared to have a concentration of about two percent alginate.

The pressure applied to the gelling precursor solution and/or the polymer solution in the drop formation process can be selected, for example, based on the desired size of the drops and/or the viscosities of the solutions. In general, for a given solution, as the size of the nozzle orifice decreases (e.g., to produce smaller particles), the pressure applied to the solution increases. For example, a pressure of about 0.5 Bar can be applied to a solution with a viscosity of about 50 centipoise that flows through an orifice with a diameter of about 300 microns. A pressure of about 0.8 Bar can be applied to the same solution with the same viscosity when the solution flows through an orifice with a diameter of about 200 microns. Generally, for a given solution flowing through an orifice of a given diameter, as the viscosity of the solution decreases, the pressure that is applied to the solution decreases. For example, a pressure of about 0.8 Bar can be applied to a solution with a viscosity of about 50 centipoise when the solution flows through an orifice with a diameter of about 200 microns. A pressure of about 0.5 Bar can be applied to the same solution when the solution flows through the same orifice, but has a different viscosity (e.g., about 25 centipoise).

In general, the distance between gelling vessel 1400 and inner orifice 1310 and/or orifice 1320 is selected so that the drops are separated before reaching vessel 1400. In some embodiments, the distance from inner orifice 1310 and/or orifice 1320 to the mixture contained in gelling vessel 1400 is from about five inches to about eight inches (e.g., from about five inches to about six inches).

In general, the polymer solution and gelling precursor solution can be formed according to any of a number of different methods. In some embodiments, the polymer solution and/or gelling precursor solution can be formed by dissolving one or more polymers and/or gelling precursors in water prior to use in drop generator 1200. The polymer can, for example, be dissolved in water by heating (e.g., above about 70° C. or more, about 121° C.). The gelling precursor can, for example, be dissolved in water at room temperature. In certain embodiments, the polymer solution and/or the gelling precursor solution can be formed by mixing water with one or more polymers and/or gelling precursors and heating the mixture in an autoclave. Heat can alternatively or additionally be applied to a mixture of water and one or more polymers and/or gelling precursors by, for example, microwave application. In some embodiments, a homogenizer (e.g., in combination with microwave application) can be used to mix the water with the polymer(s) and/or gelling precursor(s).

Generally, the polymer or polymers used in the polymer solution, and the gelling precursor or precursors used in the gelling precursor solution, are biocompatible.

Examples of polymers include polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co-glycolic) acids (e.g., poly (d-lactic-co-glycolic) acids) and copolymers or mixtures thereof. A preferred polymer is polyvinyl alcohol (PVA). The polyvinyl alcohol, in particular, is typically hydrolyzed in the range of from about 80 percent to about 99 percent. The weight average molecular weight of the base polymer can be, for example, in the range of from about 9000 to about 186,000 (e.g., from about 85,000 to about 146,000, from about 89,000 to about 98,000).

Examples of gelling precursors include alginates, alginate salts, xanthan gums, natural gum, agar, agarose, chitosan, carrageenan, fucoidan, furcellaran, laminaran, hypnea, eucheuma, gum arabic, gum ghatti, gum karaya, gum tragacanth, hyaluronic acid, locust beam gum, arabinogalactan, pectin, amylopectin, other water soluble polysaccharides and other ionically cross-linkable polymers. A particular gelling precursor is sodium alginate. A preferred sodium alginate is high guluronic acid, stem-derived alginate (e.g., about 50 percent or more, about 60 percent or more guluronic acid) with a low viscosity (e.g., from about 20 centipoise to about 80 centipoise at 20° C.), which produces a high tensile, robust gel.

The mixture contained in gelling vessel 1400 includes a gelling agent which interacts with the gelling precursor to stabilize drops by forming a stable gel. Suitable gelling agents include, for example, a charged polymer (e.g., polyacrylic acid), or a divalent cation such as alkali metal salt, alkaline earth metal salt or a transition metal salt that can ionically cross-link with the gelling precursor. An inorganic salt, for example, a calcium, barium, zinc or magnesium salt can be used as a gelling agent. In embodiments, particularly those using an alginate gelling precursor, a suitable gelling agent is calcium chloride. The calcium cations have an affinity for carboxylic groups in the gelling precursor. The cations complex with carboxylic groups in the gelling precursor, resulting in encapsulation of the polymer by the gelling precursor.

Without wishing to be bound by theory, it is believed that in some embodiments (e.g., when forming particles having a diameter of about 500 microns or less), it can be desirable to reduce the surface tension of the mixture contained in gelling vessel 1400. This can be achieved, for example, by heating the mixture in gelling vessel 1400 (e.g., to a temperature greater than room temperature, such as a temperature of about 30° C. or more (e.g., a temperature of about 80° C. or more)), by bubbling a gas (e.g., air, nitrogen, argon, krypton, helium, neon) through the mixture contained in gelling vessel 1400, by stirring (e.g., via a magnetic stirrer) the mixture contained in gelling vessel 1400, by including a surfactant in the mixture containing the gelling agent, and/or by forming a mist containing the gelling agent above the mixture contained in gelling vessel 1400 (e.g., to reduce the formation of tails and/or enhance the sphericity of the particles).

As noted above, following drop stabilization, the gelling solution can be decanted from the solid drops, or the solid drops can be removed from the gelling solution by sieving. The solid drops are then transferred to reactor vessel 1500, where the polymer in the solid drops is reacted (e.g., cross-linked) to produce particles.

Reactor vessel 1500 contains an agent that chemically reacts with the polymer to cause cross-linking between polymer chains and/or within a polymer chain. For example, in embodiments in which the polymer is polyvinyl alcohol, vessel 1500 can include one or more aldehydes, such as formaldehyde, glyoxal, benzaldehyde, aterephthalaldehyde, succinaldehyde and glutaraldehyde for the acetalization of polyvinyl alcohol. Vessel 1500 also can include an acid, for example, strong acids such as sulfuric acid, hydrochloric acid, nitric acid and weak acids such as acetic acid, formic acid and phosphoric acid. In embodiments, the reaction is primarily a 1,3-acetalization:

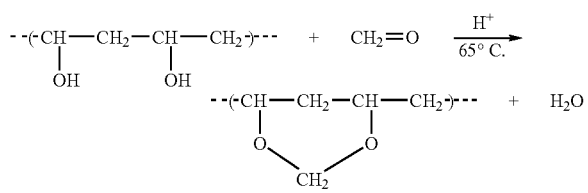

This intra-chain acetalization reaction can be carried out with relatively low probability of inter-chain cross-linking, as described in John G. Pritchard, "Poly(Vinyl Alcohol) Basic Properties and Uses (Polymer Monograph, vol. 4) (see p. 93-97), Gordon and Breach, Science Publishers Ltd., London, 1970, which is incorporated herein by reference. Because the reaction proceeds in a random fashion, some OH groups along a polymer chain might not react with adjacent groups and may remain unconverted.

Adjusting for the amounts of aldehyde and acid used, reaction time and reaction temperature can control the degree of acetalization. In embodiments, the reaction time is from about five minutes to about one hour (e.g., from about 10 minutes to about 40 minutes, about 20 minutes). The reaction temperature can be, for example, from about 25° C. to about 150° C. (e.g., from about 75° C. to about 130° C., about 65° C.). Reactor vessel 1500 can be placed in a water bath fitted with an orbital motion mixer. The particles are washed several times with deionized water to remove residual acidic solution.

Figure 3:
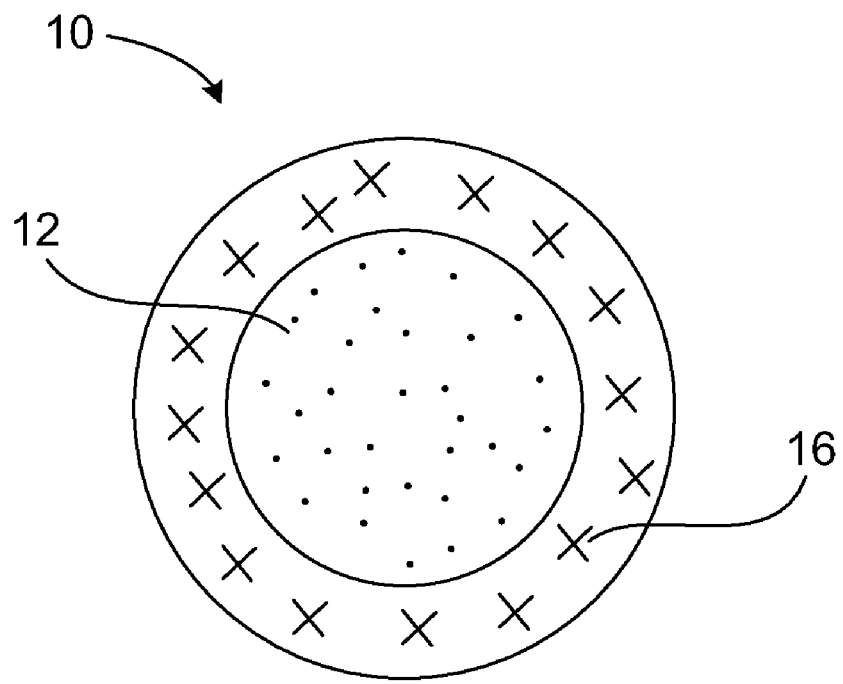
FIG. 3 is a cross-sectional view of an embodiment of a particle.

FIG. 3 shows a particle 10 that can be formed by the process noted above (without dissolving the gelling precursor). Particle 10 includes an interior region 12 formed of the polymer and an exterior region 16 formed of the gelling precursor (which is in a gelled state as explained above).

In general, particle 10 can have a diameter of from about ten microns to about 3,000 microns (e.g., from about 40 microns to about 2,000 microns; from about 100 microns to about 700 microns; from about 500 microns to about 700 microns; from about 100 microns to about 500 microns; from about 100 microns to about 300 microns; from about 300 microns to about 500 microns; from about 500 microns to about 1,200 microns; from about 500 microns to about 700 microns; from about 700 microns to about 900 microns; from about 900 microns to about 1,200 microns). In some embodiments, particle 10 can have a diameter of about 3,000 microns or less (e.g., about 2,500 microns or less; about 2,000 microns or less; about 1,500 microns or less; about 1,200 microns or less; about 1,000 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,000 microns or more; about 1,200 microns or more; about 1,500 microns or more; about 2,000 microns or more; about 2,500 microns or more).

In certain embodiments, particle 10 can have a sphericity of about 0.8 or more (e.g., about 0.85 or more, about 0.9 or more, about 0.95 or more, about 0.97 or more). The sphericity of a particle can be determined using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The system software identifies and measures particles in an image in the form of a fiber, rod or sphere. The sphericity of a particle, which is computed as Da/Dp (where Da=$\sqrt{(4A/\pi)}$; Dp=P/$\pi$; A=pixel area; P=pixel perimeter), is a value from zero to one, with one representing a perfect circle.

Figure 4:
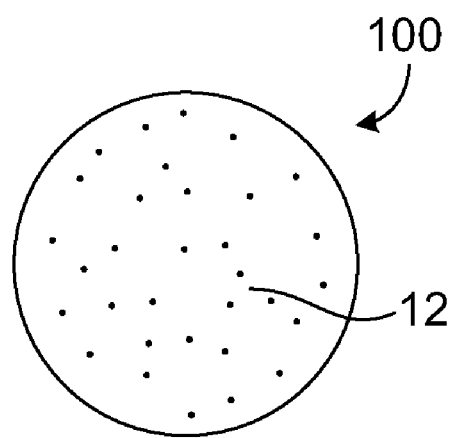
FIG. 4 is a cross-sectional view of an embodiment of a particle.

As noted above, in some embodiments, the gelling precursor (in a gelled state) is removed from particles 10 (e.g., by an ion exchange reaction), forming particles 100, shown in FIG. 4. Particles 100 include the polymer but are substantially free of the gelling precursor. In some embodiments in which the gelling precursor is formed of sodium alginate, the sodium alginate is removed by ion exchange with a solution of sodium hexa-metaphosphate (EM Science). The solution can include, for example, ethylenediaminetetracetic acid (EDTA), citric acid, other acids, and phosphates. The concentration of the sodium hexa-metaphosphate can be, for example, from about one weight percent to about 20 weight percent (e.g., from about one weight percent to about ten weight percent, about five weight percent) in deionized water. Residual gelling precursor (e.g., sodium alginate) can be measured by assay (e.g., for the detection of uronic acids in, for example, alginates containing mannuronic and guluronic acid residues). A suitable assay includes rinsing the particles with sodium tetraborate in sulfuric acid solution to extract alginate, combining the extract with metahydroxydiphenyl colormetric reagent, and determining concentration by UV/VIS spectroscopy. Testing can be carried out by alginate suppliers such as FMC Biopolymer, Oslo, Norway. Residual alginate may be present in the range of, for example, from about 20 weight percent to about 35 weight percent prior to rinsing, and in the range of from about 0.01 weight percent to about 0.5 weight percent (e.g., from about 0.1 weight percent to about 0.3 weight percent, about 0.18 weight percent) in the particles after rinsing for 30 minutes in water at about 23° C.

Figure 5:
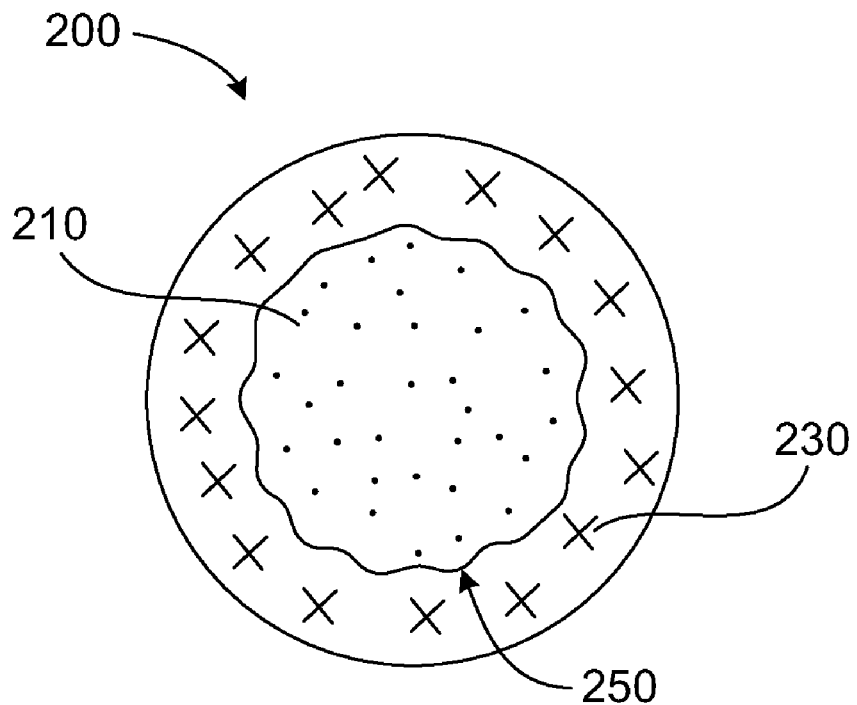
FIG. 5 is a cross-sectional view of an embodiment of a particle.
Figure 6:
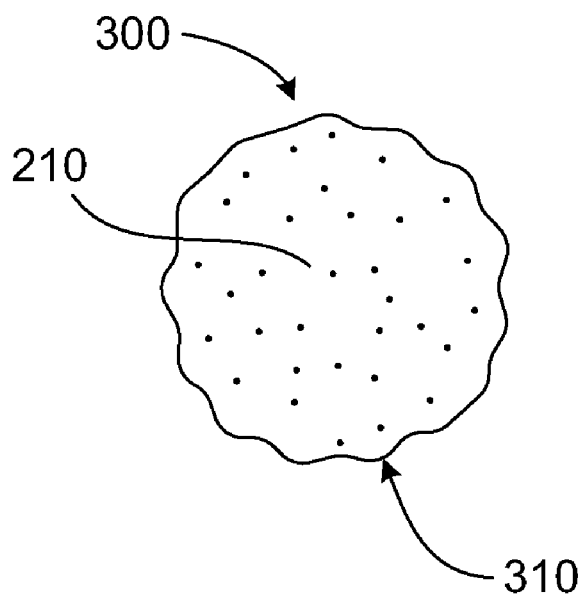
FIG. 6 is a cross-sectional view of an embodiment of a particle.

In some embodiments, and as shown in FIGS. 5 and 6, the gelling precursor can be removed from a particle to form a smaller particle with a rough surface. FIG. 5 shows a particle 200 with an interior region 210 that includes a polymer and an exterior region 230 that includes a gelling precursor. A boundary 250 between the gelling precursor and the polymer is not well-defined. Such a boundary can be formed, for example, when there is some mixing between the gelling precursor solution and the polymer solution at the interface between the two solutions during the formation of particle 200. When the gelling precursor is removed from particle 200, a particle 300 having a rough surface 310, shown in FIG. 6, can result. Particle 300 is formed substantially of the polymer and is substantially free of the gelling precursor.

As noted above, after either cross-linking or removal of the gelling precursor, the particles formed using concentric nozzle 1300 are filtered through filter 1700 to remove residual debris. Particles of from about 100 microns to about 300 microns can filtered through a sieve of about 710 microns and then a sieve of about 300 microns. The particles can then be collected on a sieve of about 20 microns. Particles of from about 300 to about 500 microns can filtered through a sieve of about 710 microns and then a sieve of about 500 microns. The particles can then be collected on a sieve of about 100 microns. Particles of from about 500 to about 700 microns can be filtered through a sieve of about 1000 microns, then filtered through a sieve of about 710 microns, and then a sieve of about 300 microns. The particles can then be collected in a catch pan. Particles of from about 700 to about 900 microns can be filtered through a sieve of 1000 microns and then a sieve of 500 microns. The particles can then be collected in a catch pan. Particles of from about 900 to about 1200 microns can filtered through a sieve of 1180 microns and then a sieve of 710 microns. The particles can then be collected in a catch pan. Other size sieves can be used if desired.

The particles are then packaged. Typically, from about one milliliter to about five milliliters of particles are packaged in from about five milliliters to about ten milliliters of saline. The filtered particles then are typically sterilized by a low temperature technique, such as e-beam irradiation. In embodiments, electron beam irradiation can be used to pharmaceutically sterilize the particles (e.g., to reduce bioburden). In e-beam sterilization, an electron beam is accelerated using magnetic and electric fields, and focused into a beam of energy. The resultant energy beam can be scanned by means of an electromagnet to produce a "curtain" of accelerated electrons. The accelerated electron beam penetrates the collection of particles, destroying bacteria and mold to sterilize and reduce the bioburden in the particles. Electron beam sterilization can be carried out by sterilization vendors such as Titan Scan, Lima, Ohio.

In some embodiments, multiple particles are combined with a carrier fluid (e.g., a pharmaceutically acceptable carrier, such as a saline solution, a contrast agent, or both) to form an embolic composition. In general, the density of the particles (e.g., as measured in grams of material per unit volume) is such that they can be readily suspended in the carrier fluid and remain suspended during delivery. In some embodiments, the density of a particle is from about 1.1 grams per cubic centimeter to about 1.4 grams per cubic centimeter. As an example, for suspension in a saline-contrast solution, the density can be from about 1.2 grams per cubic centimeter to about 1.3 grams per cubic centimeter.

Embolic compositions can be used in, for example, neural, pulmonary, and/or AAA (abdominal aortic aneurysm) applications. The compositions can be used in the treatment of, for example, fibroids, tumors, internal bleeding, arteriovenous malformations (AVMs), and/or hypervascular tumors. The compositions can be used as, for example, fillers for aneurysm sacs, AAA sac (Type II endoleaks), endoleak sealants, arterial sealants, and/or puncture sealants, and/or can be used to provide occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels, e.g. in the brain, which shunt blood from a high pressure artery to a low pressure vein, resulting in hypoxia and malnutrition of those regions from which the blood is diverted. In some embodiments, a composition containing the particles can be used to prophylactically treat a condition.

The magnitude of a dose of an embolic composition can vary based on the nature, location and severity of the condition to be treated, as well as the route of administration. A physician treating the condition, disease or disorder can determine an effective amount of embolic composition. An effective amount of embolic composition refers to the amount sufficient to result in amelioration of symptoms or a prolongation of survival of the subject. The embolic compositions can be administered as pharmaceutically acceptable compositions to a subject in any therapeutically acceptable dosage, including those administered to a subject intravenously, subcutaneously, percutaneously, intratrachealy, intramuscularly, intramucosaly, intracutaneously, intra-articularly, orally or parenterally.

An embolic composition can include a mixture of particles (e.g., particles that include different types of therapeutic agents), or can include particles that are all of the same type. In some embodiments, an embolic composition can be prepared with a calibrated concentration of particles for ease of delivery by a physician. A physician can select an embolic composition of a particular concentration based on, for example, the type of embolization procedure to be performed. In certain embodiments, a physician can use an embolic composition with a relatively high concentration of particles during one part of an embolization procedure, and an embolic composition with a relatively low concentration of particles during another part of the embolization procedure.

Suspensions of particles in saline solution can be prepared to remain stable (e.g., to remain suspended in solution and not settle and/or float) over a desired period of time. A suspension of particles can be stable, for example, for from about one minute to about 20 minutes (e.g. from about one minute to about ten minutes, from about two minutes to about seven minutes, from about three minutes to about six minutes).

In some embodiments, particles can be suspended in a physiological solution by matching the density of the solution to the density of the particles. In certain embodiments, the particles and/or the physiological solution can have a density of from about one gram per cubic centimeter to about 1.5 grams per cubic centimeter (e.g., from about 1.2 grams per cubic centimeter to about 1.4 grams per cubic centimeter, from about 1.2 grams per cubic centimeter to about 1.3 grams per cubic centimeter).

Figure 7A:
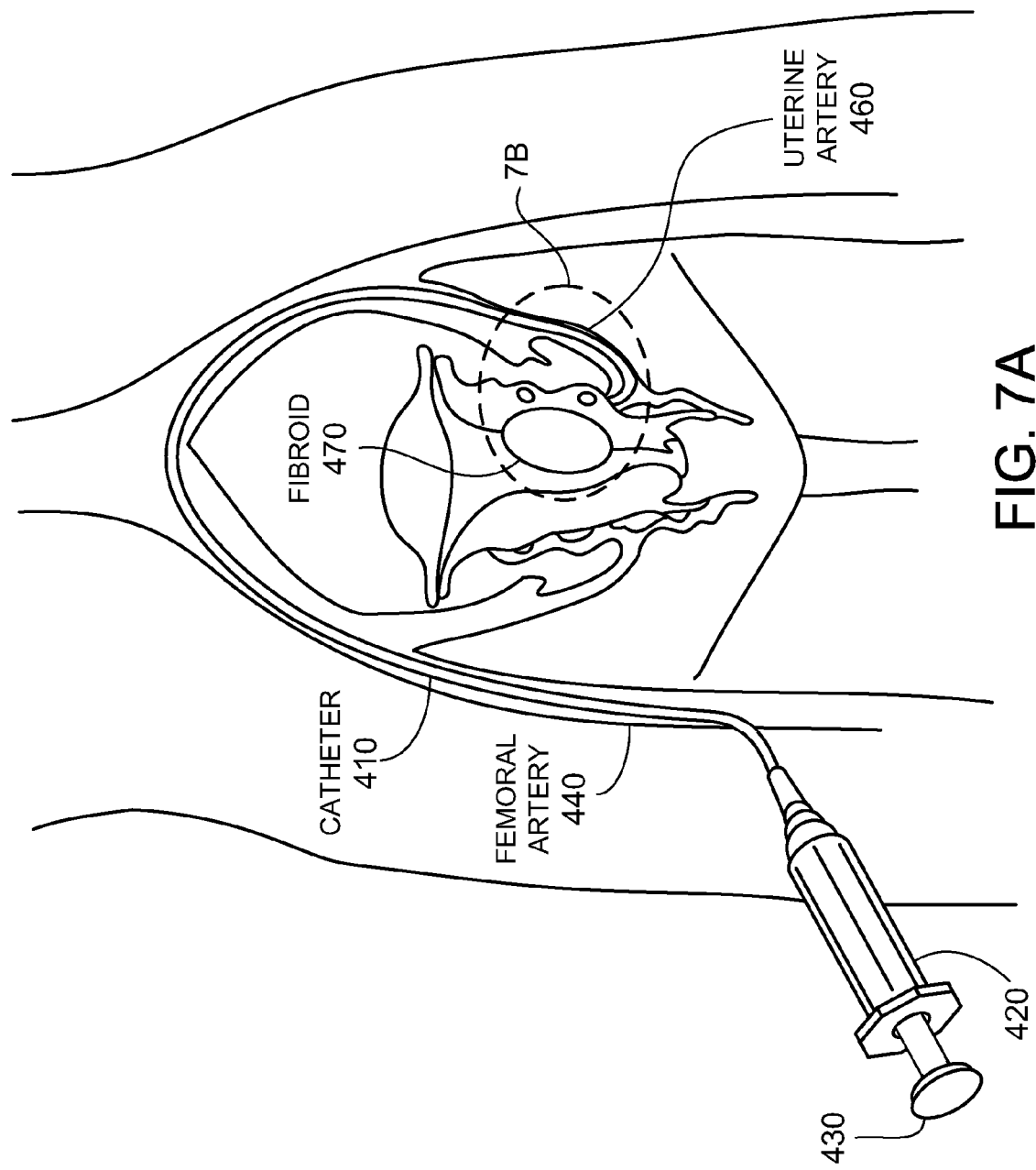
FIG. 7A is a schematic illustrating injection of an embolic composition including embolic particles into a vessel.
Figure 7B:
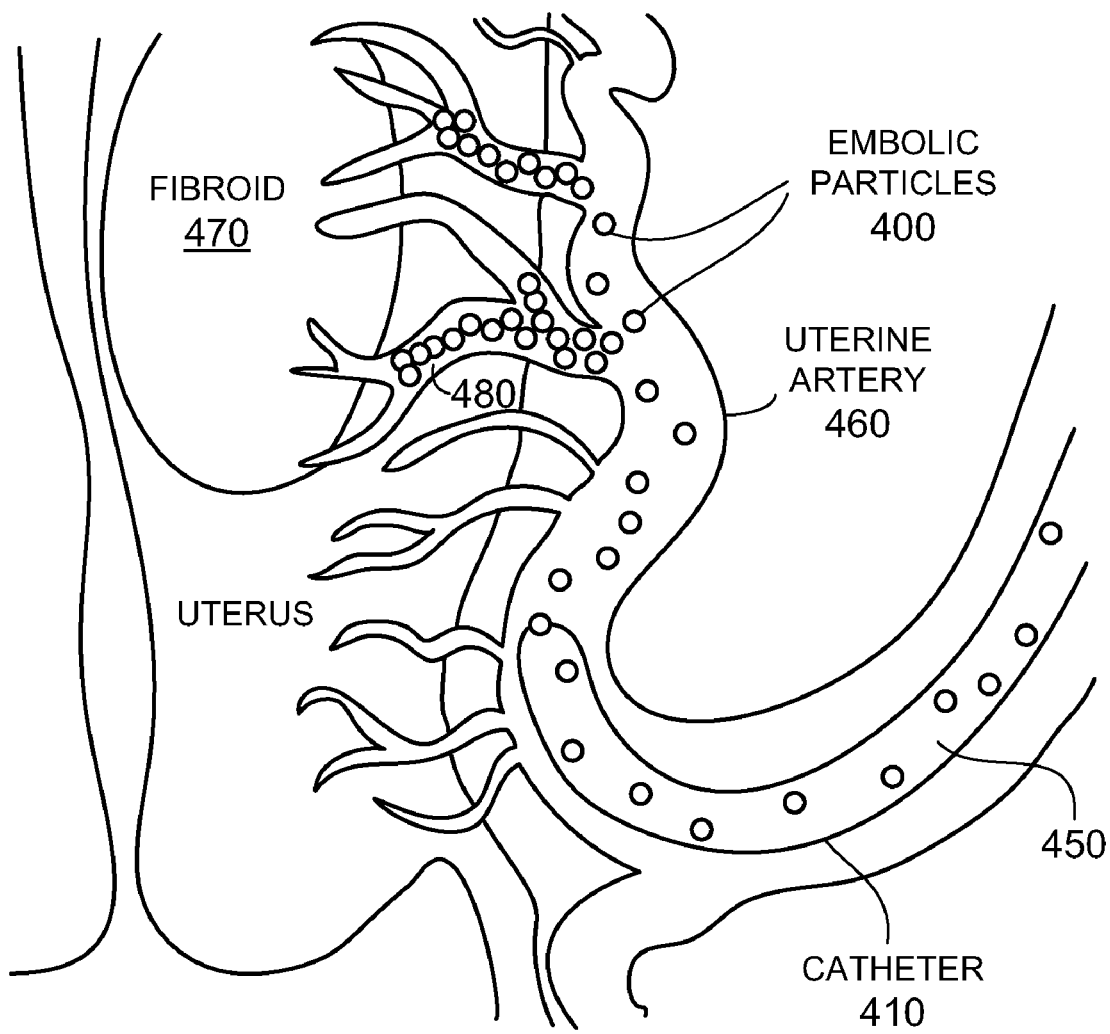
FIG. 7B is an enlarged view of region 7B in FIG. 7A.

FIGS. 7A and 7B show an embolization procedure in which an embolic composition including embolic particles 400 and a carrier fluid is injected into a vessel through an instrument such as a catheter 410. Catheter 410 is connected to a syringe barrel 420 with a plunger 430. The embolic composition is loaded into syringe barrel 420, and catheter 410 is inserted, for example, into a femoral artery 440 of a patient. Plunger 430 of syringe barrel 420 is then compressed to deliver the embolic composition through catheter 410 into a lumen 450 of a uterine artery 460 that leads to a fibroid 470 located in the uterus of the patient. The embolic composition can, for example, occlude uterine artery 460.

As shown in FIG. 7B, uterine artery 460 is subdivided into smaller uterine vessels 480 (e.g., having a diameter of about two millimeters or less) which feed fibroid 470. Particles 400 in the embolic composition partially or totally fill the lumen of uterine artery 460, either partially or completely occluding the lumen of the uterine artery 460 that feeds uterine fibroid 470.

In some embodiments, among the particles delivered to a subject in an embolic composition, the majority (e.g., about 50 percent or more, about 60 percent or more, about 70 percent or more, about 80 percent or more, about 90 percent or more) of the particles can have a diameter of about 3,000 microns or less (e.g., about 2,500 microns or less; about 2,000 microns or less; about 1,500 microns or less; about 1,200 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,200 microns or more; about 1,500 microns or more; about 2,000 microns or more; about 2,500 microns or more).

In certain embodiments, the particles delivered to a subject in an embolic composition can have an arithmetic mean diameter of from about ten microns to about 3,000 microns. In some embodiments, the particles can have an arithmetic mean diameter of about 3,000 microns or less (e.g., about 2,500 microns or less; about 2,000 microns or less; about 1,500 microns or less; about 1,200 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,200 microns or more; about 1,500 microns or more; about 2,000 microns or more; about 2,500 microns or more). Exemplary ranges for the arithmetic mean diameter of particles delivered to a subject include from about 100 microns to about 300 microns; from about 300 microns to about 500 microns; from about 500 microns to about 700 microns; and from about 900 microns to about 1,200 microns. In general, the particles delivered to a subject in an embolic composition can have an arithmetic mean diameter in approximately the middle of the range of the diameters of the individual particles, and a variance of about 20 percent or less (e.g. about 15 percent or less, about ten percent or less).

In some embodiments, the arithmetic mean diameter of the particles delivered to a subject in an embolic composition can vary depending upon the particular condition to be treated. As an example, in embodiments in which the particles in an embolic composition are used to treat a liver tumor, the particles delivered to the subject can have an arithmetic mean diameter of about 500 microns or less (e.g., from about 100 microns to about 300 microns; from about 300 microns to about 500 microns). As another example, in embodiments in which the particles in an embolic composition are used to treat a uterine fibroid, the particles delivered to the subject in an embolic composition can have an arithmetic mean diameter of about 1,200 microns or less (e.g., from about 500 microns to about 700 microns; from about 700 microns to about 900 microns; from about 900 microns to about 1,200 microns).

The arithmetic mean diameter of a group of particles can be determined using a Beckman Coulter RapidVUE Image Analyzer version 2.06 (Beckman Coulter, Miami, Fla.), described above. The arithmetic mean diameter of a group of particles (e.g., in a composition) can be determined by dividing the sum of the diameters of all of the particles in the group by the number of particles in the group.

In certain embodiments, the sphericity of a particle after compression in a catheter (e.g., after compression to about 50 percent or more of the cross-sectional area of the particle) can be about 0.8 or more (e.g., about 0.85 or more, about 0.9 or more, about 0.95 or more, about 0.97 or more). The particle can be, for example, manually compressed, essentially flattened, while wet to about 50 percent or less of its original diameter and then, upon exposure to fluid, regain a sphericity of about 0.8 or more (e.g., about 0.85 or more, about 0.9 or more, about 0.95 or more, about 0.97 or more).

Figure 8:
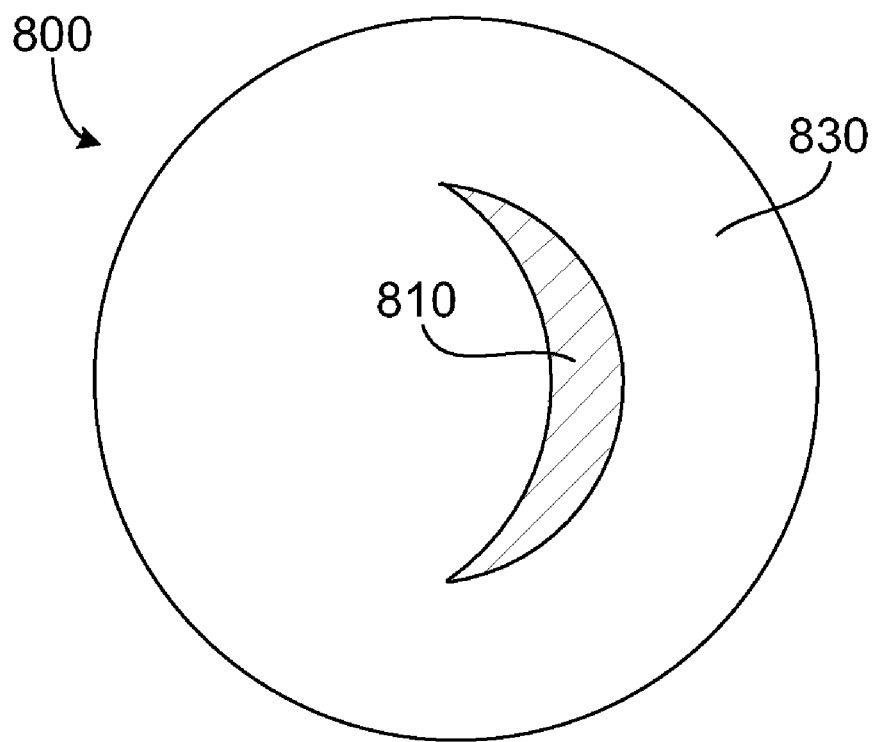
FIG. 8 is a cross-sectional view of an embodiment of a particle.
Figure 9:
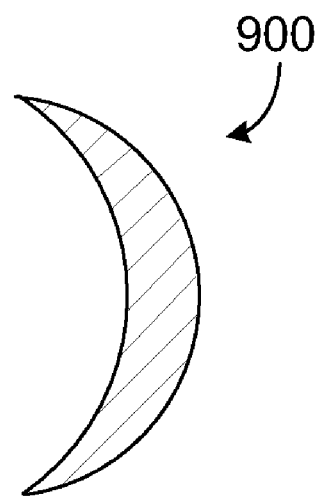
FIG. 9 is a cross-sectional view of an embodiment of a particle.

While substantially spherical particles have been shown, in some embodiments a concentric nozzle can be used to make one or more non-spherical particles. For example, a concentric nozzle can be used to make crescent-shaped particles, as shown in FIGS. 8 and 9. FIG. 8 shows a precursor particle 800, formed by a concentric nozzle. Precursor particle 800 has a crescent-shaped interior region 810 that includes a polymer, and an exterior region 830 that includes a gelling precursor. Exterior region 830 can be removed (e.g., by exposing precursor particle 800 to a gel dissolution chamber) to produce crescent-shaped particle 900, shown in FIG. 9, which is formed substantially of polymer. While precursor particles with interior crescent-shaped regions have been shown, in some embodiments precursor particles with exterior crescent-shaped regions can be formed. In certain embodiments, precursor particles with crescent-shaped regions can be formed by using a first material and a second material that has a much greater (e.g., by 50 centipoise) viscosity than the first material. In some embodiments, precursor particles with crescent-shaped regions can be formed by using a higher flow rate (e.g., about 15 milliliters per minute) for the stream that flows through one nozzle (e.g., the outer nozzle) of a concentric nozzle and a lower flow rate (e.g., about seven milliliters per minute) for the stream that flows through another nozzle (e.g., the inner nozzle) of the concentric nozzle.

Other Embodiments

While certain embodiments have been described, the invention is not so limited.

Figure 10:
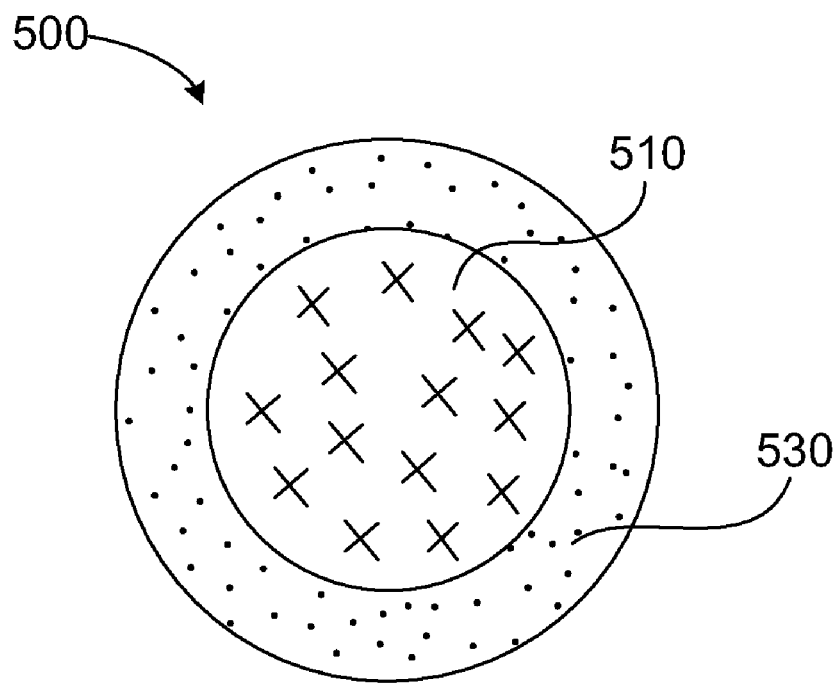
FIG. 10 is a cross-sectional view of an embodiment of a particle.
Figure 11:
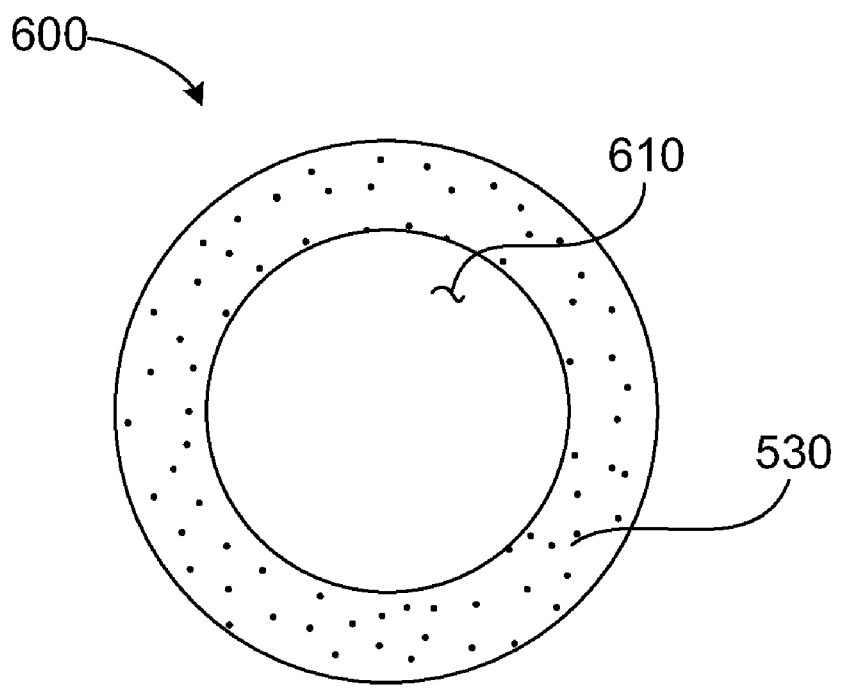
FIG. 11 is a cross-sectional view of an embodiment of a particle.

As an example, while embodiments have been described in which a polymer solution flows through the inner nozzle and a gelling precursor solution flows through the outer nozzle, in some embodiments, a polymer solution flows through the outer nozzle and a gelling precursor solution flows through the inner nozzle. If the gelling precursor is not dissolved, the resulting particles can have, for example, an interior region formed of gelling precursor (in a gelled state) and an exterior region formed of polymer. FIG. 10 shows such a particle 500 having an interior region 510 formed of gelling precursor (in a gelled state) and an exterior region 530 formed of polymer. If the gelling precursor is dissolved, the resulting particles can have, for example, a hollow interior and an exterior region formed of polymer. FIG. 11 shows such a particle 600 having a hollow interior region 610 and exterior region 530 (formed of polymer). In certain embodiments, particle 600 can be used to deliver one or more agents (e.g., therapeutic agents) into the body (see discussion below). For example, the agent(s) can be injected into hollow interior region 610 of particle 600 prior to delivery.

As another example, while embodiments of a concentric nozzle having two nozzles have been described, other embodiments are possible. In general, a concentric nozzle can have more than two (e.g., three, four, five, six, seven, eight, nine, ten) nozzles. Typically, each nozzle in a concentric nozzle has a stream of a particular material that flows therethrough. In some embodiments, however, a stream of a particular material may flow through more than one nozzle.

As a further example, in some embodiments drops may be formed without vibrating the concentric nozzle. In certain embodiments, drops can be formed by establishing an electrostatic potential between concentric nozzle 1300 and gelling vessel 1400 so that the streams exiting concentric nozzle 1300 are pulled toward gelling vessel 1400, thereby forming drops. An electrostatic potential can be established, for example, by charging concentric nozzle 1300 and charging gelling vessel 1400 with the opposite charge. For example, concentric nozzle 1300 can be negatively charged and gelling vessel 1400 can be positively charged. An example of a commercially available drop generator that forms drops by the use of an electrostatic potential is the NISCO Encapsulation unit VAR V1 (NISCO Engineering, Zurich, Switzerland). In some embodiments, drops can be formed by using a drop generator that employs both an electrostatic potential and a periodic disturbance (e.g., vibration of the concentric nozzle). In certain embodiments, drops can be formed by mechanically breaking the streams exiting concentric nozzle 1300 into drops 1370 (e.g., by a jet cutter). Optionally, drops may be formed by using a combination of vibration techniques and/or mechanical break-up techniques and/or electrostatic techniques.

As an additional example, in some embodiments, drop generator 1200 can charge drops 1370 after formation and prior to contact with the gelling agent, such that mutual repulsion between drops 1370 prevents drop aggregation as the drops travel from drop generator 1200 to gelling vessel 1400. Charging may be achieved, for example, by an electrostatic charging device such as a charged ring positioned downstream of concentric nozzle 1300.

As an additional example, while the formation of crescent-shaped particles has been described, in some embodiments, a drop generation process can be performed in a way that limits the likelihood of forming crescent-shaped particles and/or particles with crescent-shaped regions. For example, a polymer solution that flows through the volume defined by an inner nozzle of a concentric nozzle can include a relatively small concentration (e.g., up to about one percent) of a gelling agent (e.g., calcium ions). The presence of gelling agent in the polymer solution can reduce the likelihood of formation of particles with crescent-shaped regions (such as precursor particle 800 in FIG. 8). While not being bound by theory, it is believed that the gelling agent in the polymer solution can cause the polymer to begin to gel prior to the formation of a drop containing the polymer. If, for example, a gelling precursor solution is flowing through the outer nozzle of the concentric nozzle, then when the drop that is formed contacts gelling agent, both the interior region and the exterior region of the drop may gel. Thus, the drop can be gelling from both the inside out and the outside in. Such gelling may result in particles in which both the interior regions and the exterior regions are substantially spherical.

As another example, in certain embodiments, one or more of the materials that flow through one or more of the orifices in a concentric nozzle can be a therapeutic agent (e.g., drug), such that particles formed by the concentric nozzle incorporate the therapeutic agent(s). Alternatively or additionally, one or more therapeutic agents can be added to the particles after forming the particles. In some embodiments, a therapeutic agent can be added to a particle by, e.g., injection of the therapeutic agent into the particle and/or by soaking the particle in the therapeutic agent. Therapeutic agents include agents that are negatively charged, positively charged, amphoteric, or neutral. Therapeutic agents can be, for example, materials that are biologically active to treat physiological conditions; pharmaceutically active compounds; gene therapies; nucleic acids with and without carrier vectors; oligonucleotides; gene/vector systems; DNA chimeras; compacting agents (e.g., DNA compacting agents); viruses; polymers; hyaluronic acid; proteins (e.g., enzymes such as ribozymes); cells (of human origin, from an animal source, or genetically engineered); stem cells; immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); anti-inflammatory agents; calcium entry blockers; antineoplastic/antiproliferative/antimitotic agents (e.g., paclitaxel, doxorubicin, cisplatin); antimicrobials; anesthetic agents; anti-coagulants; vascular cell growth promoters; vascular cell growth inhibitors; cholesterol-lowering agents; vasodilating agents; agents which interfere with endogenous vasoactive mechanisms; and survival genes which protect against cell death. In some embodiments, release of a therapeutic agent from a particle can be triggered by one or more factors. For example, release of a therapeutic agent can be triggered by pH, ions, and/or temperature. Therapeutic agents are described, for example, in co-pending U.S. Patent Application Publication No. US 2004/0076582 A1, published on Apr. 22, 2004, which is incorporated herein by reference.

As an additional example, in some embodiments, one or more of the materials that flows through one or more of the orifices in a concentric nozzle can be a diagnostic agent (e.g., a radiopaque material, a material that is visible by magnetic resonance imaging (an MRI-visible material), an ultrasound contrast agent). In some embodiments, one or more of the materials used in concentric nozzle can be a ferromagnetic material. Alternatively or additionally, one or more diagnostic agents and/or ferromagnetic materials can be added to the particles after forming the particles. In some embodiments, a diagnostic agent and/or ferromagnetic material can be added to a particle by, e.g., injection of the diagnostic agent and/or ferromagnetic material into the particle and/or by soaking the particle in the diagnostic agent and/or ferromagnetic material. Diagnostic agents and ferromagnetic materials are described in U.S. Patent Application Publication No. US 2004/0101564 A1, published on May 27, 2004, and entitled "Embolization", which is incorporated herein by reference.

As another example, in certain embodiments, one or more of the materials that flow through one or more of the orifices in a concentric nozzle can be a shape memory material, which is capable of being configured to remember (e.g., to change to) a predetermined configuration or shape. In some embodiments, particles that include a shape memory material can be selectively transitioned from a first state to a second state. For example, a heating device provided in the interior of a delivery catheter can be used to cause a particle including a shape memory material to transition from a first state to a second state. Shape memory materials and particles that include shape memory materials are described in, for example, U.S. Patent Application Publication No. US 2004/0091543 A1, published on May 13, 2004, and U.S. patent application Ser. No. 10/791,103, filed Mar. 2, 2004, and entitled "Embolic Compositions", both of which are incorporated herein by reference.

As an additional example, in some embodiments, one or more of the materials that flow through one or more of the orifices in a concentric nozzle can be a surface preferential material. Surface preferential materials are described, for example, in U.S. patent application Ser. No. 10/791,552, filed on Mar. 2, 2004, and entitled "Embolization", which is incorporated herein by reference.

As a further example, in certain embodiments, a particle can be coated (e.g., with a bioabsorbable material). For example, a particle can have an interior region including a radiopaque material, an exterior region including a polymer, and a hydrogel coating over the exterior region. The coating can contain, for example, one or more therapeutic agents. In certain embodiments, a particle can be coated to include a high concentration of one or more therapeutic agents and/or one or more of the therapeutic agents can be loaded into the interior of the particle. The surface of the particle can release an initial dosage of therapeutic agent after which the body of the particle can provide a burst release of therapeutic agent. The therapeutic agent on the surface of the particle can be the same as or different from the therapeutic agent in the body of the particle. The therapeutic agent on the surface can be applied by exposing the particle to a high concentration solution of the therapeutic agent. The therapeutic agent coated particle can include another coating over the surface the therapeutic agent (e.g., a degradable and/or bioabsorbable polymer which erodes when the particle is administered). The coating can assist in controlling the rate at which therapeutic agent is released from the particle. For example, the coating can be in the form of a porous membrane. The coating can delay an initial burst of therapeutic agent release. The coating can be applied by dipping or spraying the particle. The erodible polymer can be a polysaccharide (such as an alginate). In some embodiments, the coating can be an inorganic, ionic salt. Other erodible coatings include water soluble polymers (such as polyvinyl alcohol, e.g., that has not been cross-linked), biodegradable poly DL-lactide-poly ethylene glycol (PELA), hydrogels (e.g., polyacrylic acid, haluronic acid, gelatin, carboxymethyl cellulose), polyethylene glycols (PEG), chitosan, polyesters (e.g., polycaprolactones), and poly(lactic-co-glycolic) acids (e.g., poly(d-lactic-co-glycolic) acids). The coating can include therapeutic agent or can be substantially free of therapeutic agent. The therapeutic agent in the coating can be the same as or different from an agent on a surface layer of the particle and/or within the particle. A polymer coating, e.g. an erodible coating, can be applied to the particle surface in embodiments in which a high concentration of therapeutic agent has not been applied to the particle surface. Coatings are described, for example, in U.S. Patent Application Publication No. US 2004/0076582 A1, published on Apr. 22, 2004, which is incorporated herein by reference.

As an additional example, in certain embodiments, one or more of the materials that flows through one or more of the orifices in a concentric nozzle can be bioerodible, such that the materials can eventually break down in the body and either be dispersed throughout the body or excreted from the body. A bioerodible material can be, for example, a polysaccharide (such as an alginate); a polysaccharide derivative; an inorganic, ionic salt; a water soluble polymer (such as a polyvinyl alcohol, e.g., that has not been cross-linked); biodegradable poly DL-lactide-poly ethylene glycol (PELA); a hydrogel (e.g., polyacrylic acid, haluronic acid, gelatin, carboxymethyl cellulose); a polyethylene glycol (PEG); chitosan; a polyester (e.g., a polycaprolactone); a poly(lactic-co-glycolic) acid (e.g., a poly(d-lactic-co-glycolic) acid); or a combination thereof.

As a further example, in some embodiments, a particle produced by a concentric nozzle can include one of the following combinations of materials: an interior region including a ferromagnetic material (e.g., iron, an iron oxide (e.g., $Fe_3O_4$), magnetite, a ferrofluid) and an exterior region including a polymer (e.g., a polysaccharide); an interior region including one type of therapeutic agent and an exterior region including a different type of therapeutic agent; or an interior region that includes a ferromagnetic material and an exterior region that includes a combination of a polymer and a gelling precursor.

As another example, in some embodiments the materials used in a concentric nozzle to form particles can be selected based on their immiscibility, such that streams of the materials can remain substantially discrete as they flow through drop generator 1200. In such embodiments, the streams can produce particles having an exterior region of substantially one material and an interior region of substantially another material.

As an additional example, in some embodiments, one or more of the solutions that flows through one or more of the orifices in a concentric nozzle can be chilled prior to entering the concentric nozzle (e.g., to affect the viscosity and/or flow rate of the solution).

As a further example, in certain embodiments, the materials that flow through a concentric nozzle can be selected to mix with each other upon contact. For example, one material can be a ferromagnetic material, while the other material is polyvinyl alcohol.

As another example, while concentric nozzles have been described that have two orifices, in some embodiments a concentric nozzle can include more than two orifices (e.g., three orifices, four orifices, five orifices).

Figure 12:
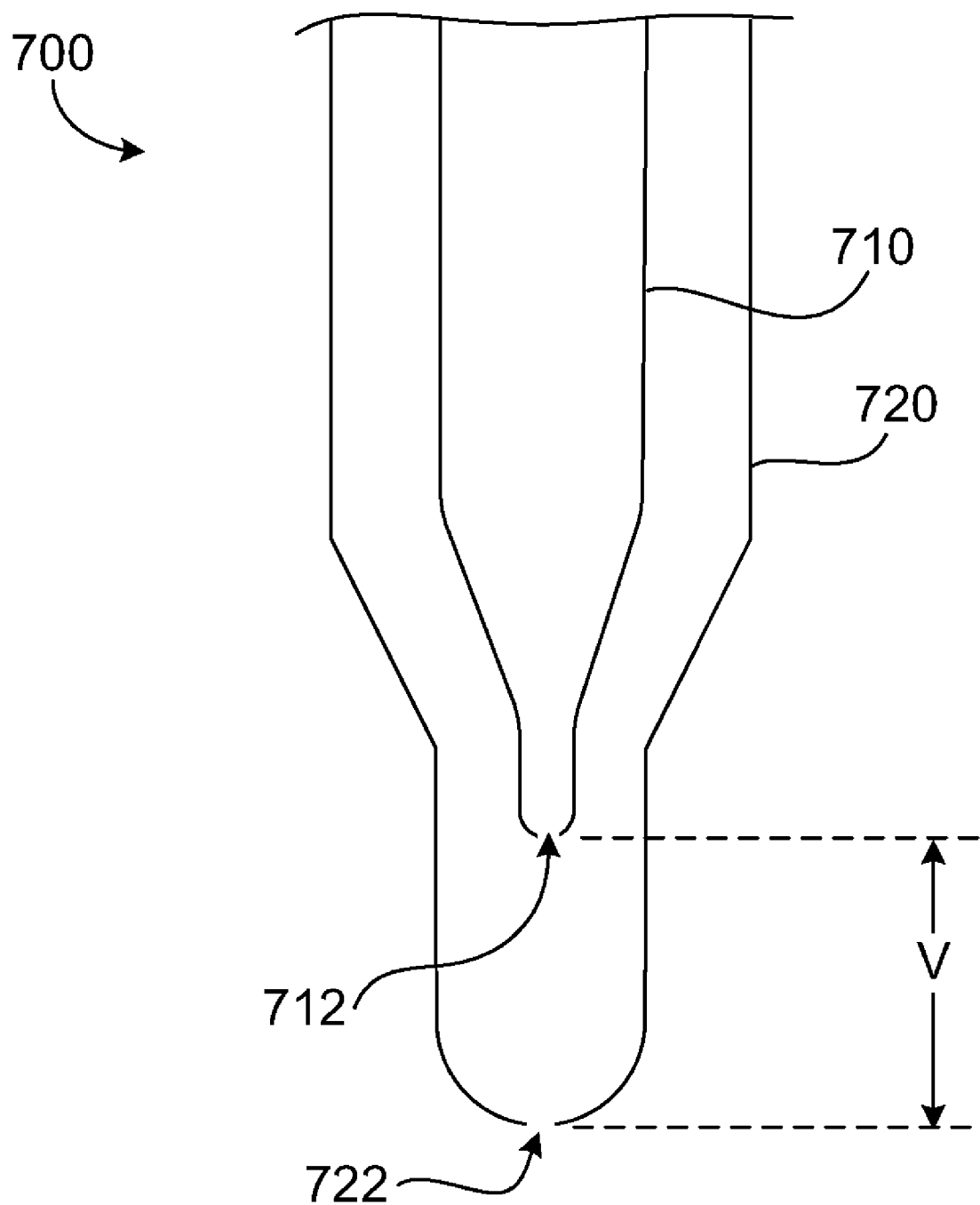
FIG. 12 is a cross-sectional view of an embodiment of an apparatus for producing particles.

As an additional example, in certain embodiments, the orifices in a concentric nozzle can be vertically spaced apart from each other. For example, FIG. 12 shows a concentric nozzle 700 that includes an inner nozzle 710 concentrically disposed within an outer nozzle 720. Inner nozzle 710 has an inner orifice 712, and outer nozzle 720 has an outer orifice 722. Inner orifice 712 is separated from outer orifice 722 by a vertical distance "V", which can be from about 0.5 millimeter to about two millimeters (e.g., about one millimeter). In some embodiments, vertical displacement of the orifices of a concentric nozzle can enhance mixing of the solutions flowing through the nozzle prior to the point at which the solutions contact the gelling agent. In such embodiments, drops formed by the nozzle can include a mixture of the solutions. In certain embodiments, mixing of the solutions within the concentric nozzle can be enhanced by starting to flow one of the solutions through the outer nozzle of the concentric nozzle prior to starting to flow the other solution through the inner nozzle of the concentric nozzle.

As another example, in some embodiments, the particles can be mechanically shaped during or after the particle formation process to be nonspherical (e.g., ellipsoidal). In certain embodiments, one or more particles can be shaped (e.g., molded, compressed, punched, and/or agglomerated with other particles) at different points in the particle manufacturing process. In some embodiments (e.g., where the polymer is a polyvinyl alcohol and the gelling precursor is sodium alginate), after contacting the particles with the gelling agent but before cross-linking, the particles can be physically deformed into a specific shape and/or size. After shaping, the polymer (e.g., polyvinyl alcohol) can be cross-linked, optionally followed by substantial removal of the gelling precursor (e.g., alginate). While substantially spherical particles are preferred, non-spherical particles can be manufactured and formed by controlling, for example, drop formation conditions. In some embodiments, nonspherical particles can be formed by post-processing the particles (e.g., by cutting or dicing into other shapes). Particle shaping is described, for example, in co-pending U.S. Patent Application Publication No. US 2003/0203985 A1, published on Oct. 30, 2003, which is incorporated herein by reference.

As a further example, in some embodiments, particles having different shapes, sizes, physical properties, and/or chemical properties, can be used together in an embolization procedure. The different particles can be delivered into the body of a subject in a predetermined sequence or simultaneously. In certain embodiments, mixtures of different particles can be delivered using a multi-lumen catheter and/or syringe. In some embodiments, particles having different shapes and/or sizes can be capable of interacting synergistically (e.g., by engaging or interlocking) to form a well-packed occlusion, thereby enhancing embolization. Particles with different shapes, sizes, physical properties, and/or chemical properties, and methods of embolization using such particles are described, for example, in U.S. Patent Application Publication No. US 2004/0091543 A1, published on May 13, 2004, and in U.S. patent application Ser. No. 10/791,103, filed Mar. 2, 2004, and entitled "Embolic Compositions", both of which are incorporated herein by reference.

As an additional example, in some embodiments the particles can be used for tissue bulking. As an example, the particles can be placed (e.g., injected) into tissue adjacent to a body passageway. The particles can narrow the passageway, thereby providing bulk and allowing the tissue to constrict the passageway more easily. The particles can be placed in the tissue according to a number of different methods, for example, percutaneously, laparoscopically, and/or through a catheter. In certain embodiments, a cavity can be formed in the tissue, and the particles can be placed in the cavity. Particle tissue bulking can be used to treat, for example, intrinsic sphincteric deficiency (ISD), vesicoureteral reflux, gastroesophageal reflux disease (GERD), and/or vocal cord paralysis (e.g., to restore glottic competence in cases of paralytic dysphonia). In some embodiments, particle tissue bulking can be used to treat urinary incontinence and/or fecal incontinence. The particles can be used as a graft material or a filler to fill and/or to smooth out soft tissue defects, such as for reconstructive or cosmetic applications (e.g., surgery). Examples of soft tissue defect applications include cleft lips, scars (e.g., depressed scars from chicken pox or acne scars), indentations resulting from liposuction, wrinkles (e.g., glabella frown wrinkles), and soft tissue augmentation of thin lips. Tissue bulking is described, for example, in co-pending U.S. Patent Application Publication No. US 2003/0233150 A1, published on Dec. 18, 2003, which is incorporated herein by reference.

As a further example, in some embodiments a particle can be porous and/or can include one or more cavities. In certain embodiments, the particle can have a substantially uniform pore structure. In some embodiments, the particle can have a non-uniform pore structure. For example, the particle can have a substantially non-porous interior region (e.g., formed of a polyvinyl alcohol) and a porous exterior region (e.g., formed of a mixture of a polyvinyl alcohol and alginate). Porous particles are described in U.S. Published Patent Application No. US 2004/0096662 A1, published on May 20, 2004, which is incorporated herein by reference.

As another example, in some embodiments a solution can be added to the concentric nozzle to enhance the porosity of particles produced by the concentric nozzle. Examples of porosity-enhancing solutions include starch, sodium chloride at a relatively high concentration (e.g., more than about 0.9 percent, from about one percent to about five percent, from about one percent to about two percent), and calcium chloride (e.g., at a concentration of at least about 50 mM). For example, calcium chloride can be added to a sodium alginate gelling precursor solution to increase the porosity of the particles produced from the solution.

As an additional example, in certain embodiments, the particles that are produced by a concentric nozzle can be linked together to form particle chains. For example, the particles can be connected to each other by links that are formed of one or more of the same material(s) as the particles, or of one or more different material(s) from the particles. Alternatively or additionally, the concentric nozzle can be used to form particle chains. For example, the vibration frequency of the concentric nozzle can be selected to cause the concentric nozzle to form particle chains. Particle chains and methods of making particle chains are described, for example, in U.S. patent application Ser. No. 10/830,195, filed on Apr. 22, 2004, and entitled "Embolization", which is incorporated herein by reference.

Other embodiments are in the claims.

What is claimed is:

1. A method of making particles, the method comprising:
    flowing a first material through a first orifice defined by a nozzle to form a first stream comprising the first fluid;
    flowing a second material comprising a gelling precursor through a second orifice defined by the nozzle to form a second stream comprising the second fluid;
    combining the first and second streams;
    exposing the combined first and second streams to a periodic disturbance to form drops comprising the first and second materials; and
    forming particles from the drops, the particles comprising the first and second materials, wherein forming the particles includes converting the gelling precursor from a solution into a gel, and the method further comprises removing at least some of the gel from the particles.

2. The method of claim 1, wherein the particles have an arithmetic mean diameter of from about ten microns to about 3,000 microns.

3. The method of claim 1, wherein the first orifice has a diameter of from about 50 microns to about 1,000 microns.

4. The method of claim 1, wherein the first orifice has a diameter of from about 50 microns to about 300 microns.

5. The method of claim 1, wherein the second orifice has a diameter of from about 50 microns to about 1,000 microns.

6. The method of claim 1, wherein the first orifice has a first diameter, the second orifice has a second diameter, and the difference between the first and second diameters is at least about 50 microns.

7. The method of claim 1, wherein the first orifice is disposed within the second orifice.

8. The method of claim 7, wherein the first orifice and the second orifice are concentric.

9. The method of claim 8, wherein the first orifice is disposed at a vertical distance of about one millimeter from the second orifice.

10. The method of claim 1, wherein the first material flows through the first orifice at a rate of from about two milliliters per minute to about ten milliliters per minute.

11. The method of claim 10, wherein the second material flows through the second orifice at a rate of from about two milliliters per minute to about 20 milliliters per minute.

12. The method of claim 1, wherein the first material comprises a polymer.

13. The method of claim 1, wherein the first material and the second material are immiscible.

14. The method of claim 1, wherein the first stream and the second stream are concentric.

15. The method of claim 1, wherein the first material forms an interior region of the drops and the second material forms a surface region of the drops.

16. The method of claim 1, wherein a viscosity of the first material is greater than a viscosity of the second material.

17. The method of claim 1, wherein a viscosity of the second material is greater than a viscosity of the first material.

18. The method of claim 1, wherein the particles contain pores.

19. The method of claim 18, wherein the particles have a first density of pores in an interior region and a second density of pores at a surface region, the first density being different from the second density.

20. The method of claim 19, wherein the first density is greater than the second density.

21. The method of claim 18, wherein the particles have a first average pore size in an interior region and a second average pore size at a surface region, the first average pore size being different from the second average pore size.

22. The method of claim 21, wherein the first average pore size is greater than the second average pore size.

23. The method of claim 1, wherein the periodic disturbance is provided by vibrating the plurality of streams.

24. The method of claim 1, wherein forming the drops includes establishing an electrostatic potential between the first and second streams and a vessel configured to receive the drops.

25. A method of making particles, the method comprising:
flowing a polymer through a first orifice defined by a nozzle to form a first stream comprising the first fluid;
flowing a gelling precursor through a second orifice defined by the nozzle to form a second stream comprising the second fluid;
combining the first and second streams;
exposing the combined first and second streams to a periodic disturbance to form drops comprising the polymer and the gelling precursor; and
contacting the drops with a gelling agent to convert the gelling precursor to a gel, thereby providing particles comprising the polymer and the gel.

26. The method of claim 25, wherein the particles have an arithmetic mean diameter of from about ten microns to about 3,000 microns.

27. The method of claim 25, wherein the polymer comprises polyvinyl alcohol.

28. The method of claim 25, further comprising cross-linking the polymer contained in the particles.

29. The method of claim 28, further comprising, after cross-linking the polymer contained in the particles, removing the gel from the particles.

30. The method of claim 29, wherein the polymer comprises polyvinyl alcohol.

31. A method of making particles, the method comprising:
flowing polyvinyl alcohol through a first orifice defined by a nozzle to form a first stream comprising the first fluid;
flowing a gelling precursor through a second orifice defined by the nozzle to form a second stream comprising the second fluid;
combining the first and second streams;
exposing the combined first and second streams to a periodic disturbance to form drops comprising the polyvinyl alcohol and the gelling precursor;
contacting the drops with a gelling agent to convert the gelling precursor to a gel and form particles comprising the polyvinyl alcohol and the gel;
cross-linking the polyvinyl alcohol in the particles;
removing the gel from the particles to provide particles having pores,
wherein the particles having pores have an arithmetic mean diameter of from about ten microns to about 3,000 microns.

* * * * *